United States Patent
Vattiat et al.

(10) Patent No.: US 8,013,994 B1
(45) Date of Patent: Sep. 6, 2011

(54) PARTICLE STATE AND FLUX SENSOR

(75) Inventors: Brian Louis Vattiat, Austin, TX (US); Donald Edward Wroblewsky, Wellesley, MA (US); Michael Alan Gevelber, Auburndale, MA (US)

(73) Assignee: Cyber Materials LLC, Auburndale, MA (US)

( * ) Notice: Subject to any disclaimer, the term of this patent is extended or adjusted under 35 U.S.C. 154(b) by 855 days.

(21) Appl. No.: 12/008,787

(22) Filed: Jan. 14, 2008

Related U.S. Application Data

(60) Provisional application No. 60/880,274, filed on Jan. 12, 2007.

(51) Int. Cl.
*G01N 15/02* (2006.01)

(52) U.S. Cl. .............. 356/335; 219/121.36; 219/121.48; 219/121.59; 356/343

(58) Field of Classification Search .............. 219/121.1, 219/121.36, 121.47, 121.48, 121.5, 121.51, 219/121.54, 121.59; 356/335–343
See application file for complete search history.

(56) References Cited

U.S. PATENT DOCUMENTS 6,049,382 A * 4/2000 Lazaro Gomez ............. 356/336
6,967,304 B2 * 11/2005 Gevelber et al. ......... 219/121.55

* cited by examiner

*Primary Examiner* — Gregory J Toatley
*Assistant Examiner* — Iyabo S Alli
(74) *Attorney, Agent, or Firm* — James Marc Leas

(57) ABSTRACT

A method of measuring parameters of a particle includes providing a particle, wherein the particle has a first portion and a second portion. The process includes providing a column of photo-detectors including a first photo-detector and a second photo-detector, wherein the first photo-detector and the second photo-detector are sensitive to the same range of light frequencies. Light is projected from the particle onto the column of photo-detectors wherein the column of photo-detectors is oriented so the light from the first portion is projected onto the first photo-detector and light from the second portion is projected onto the second photo-detector. Light measured by the first photo-detector differs from light measured by the second photo-detector. The process further includes using the different first and the second photo-detector measurements to determine at least one from the group consisting of particle temperature and particle diameter.

36 Claims, 15 Drawing Sheets image signal

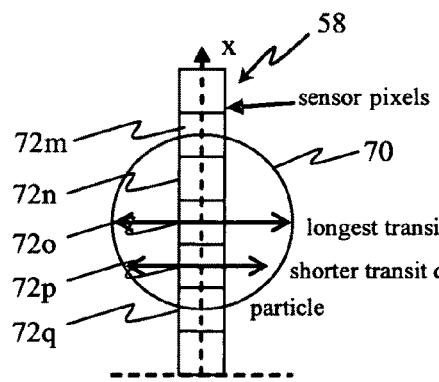
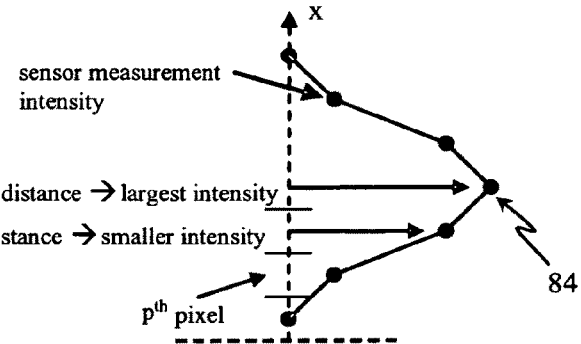
FIG.7a  FIG.7b
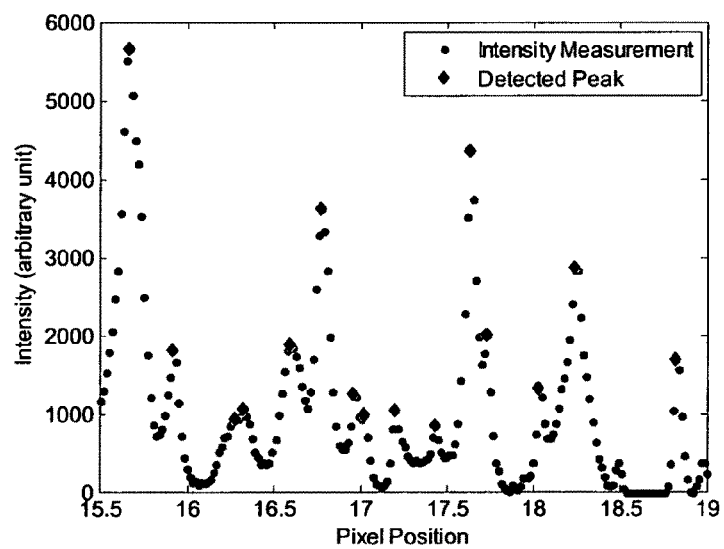
FIG.8

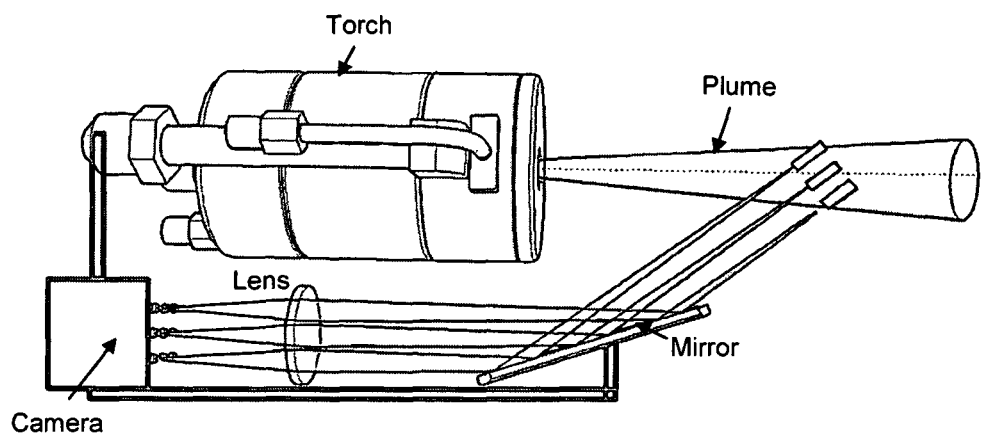
FIG.18
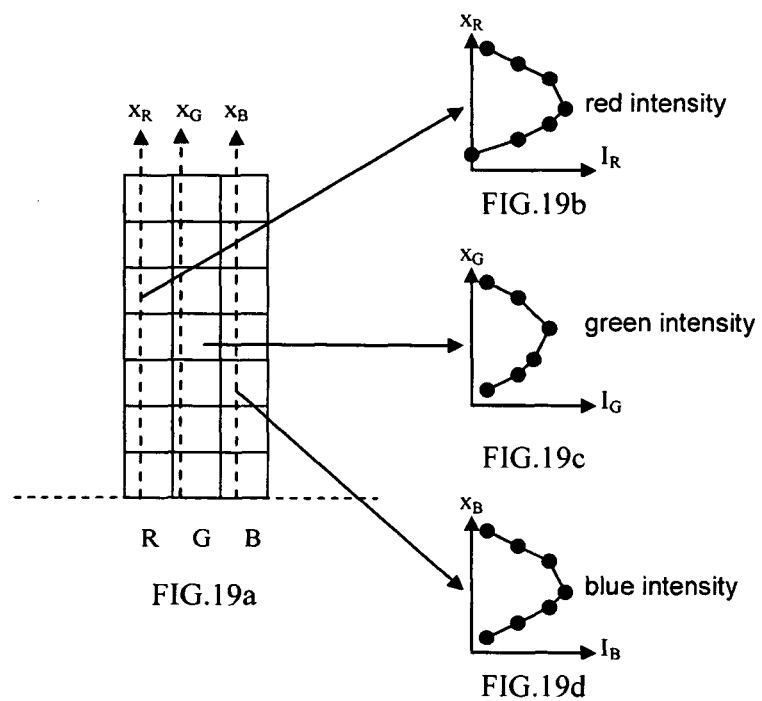
FIG.19a
FIG.19b
FIG.19c
FIG.19d

PARTICLE STATE AND FLUX SENSOR

RELATED APPLICATION AND PRIORITY

This application claims priority of Provisional U.S. Patent Application 60/880,274 filed Jan. 12, 2007, incorporated herein by reference.

This invention was made with Government Support under Contract Nos. DMI-0300484 and 011-0539622 awarded by the National Science Foundation. The Government has certain rights in the invention.

FIELD

This patent application generally relates to a particle sensor. More particularly, it relates to a system for measuring the state of particles. More particularly, it relates to a system for measuring the state of particles entrained in a plasma jet. Even more particularly, it relates to a system for measuring the state of particles entrained in a plasma jet for coating a substrate.

BACKGROUND

Thermal spray deposition is widely used to form coatings of a material on a substrate such as ceramic thermal barrier coatings (TBC) for gas turbines for power generation and aircraft engines. In the process, particles of powerdered feedstock material are entrained in a jet of high temperature gas or plasma directed at the substrate. The current coating practice is to spray feedstock material particles on a target part for a predetermined length of time. Thickness of the coating on the target part is then measured to determine if sufficient material has been applied. Parts which do not meet the quality specification (including thickness) must then undergo rework. Variations in the coating thickness from part to party have typically been due to torch aging and other variations of the deposition process.

Thermal spray processes have used a torch that produces a high-speed, high temperature jet of gas or plasma. When feedstock particles have been entrained in the jet with an injector mechanism, they both quickly accelerate toward the target and heat by absorbing thermal energy from the jet gas or plasma.

The trajectory any given particle follows once entrained in the jet is a function of the size of that particular particle, the initial velocity of the particle upon entering the jet, and state of the jet at that instant in time. These factors, however, vary from particle-to-particle and rapidly fluctuate with time. For example, Zirconia particles are typically supplied as a powder with diameters ranging from 10 µm to 90 µm and exhibit trajectories which deviate from the centerline of the jet by about 10 mm. Particle temperatures within the plume typically range from 100° C. to 4000 C. However, since the melting temperature of Zirconia is approximately 2700 C, many particles will not melt and will therefore not adhere to the target part. Instead they will strike the target and bounce off.

Therefore, the situation exists where a large but unknown number of particles are present throughout a relatively large region of space and only some of them will end up contributing to the coating. Moreover, since the particles present in the plume at any one time may consist of a large range in diameter, not all particles will contribute the same volume to the coating.

The need for improved control comes from the variation in coating thickness and density observed by applicants in over 400 hours of production runs using a prior art manufacturing deposition process. In this process, flat substrates were sprayed with yttria stabilized zirconia at least once per shift in a manufacturing environment to provide a lower bound measurement of process variation. Variations of +/−15%, with an 8% standard deviation in coating thickness'were observed, as shown in FIG. 1. In the graph dotted vertical lines indicate torch rebuilds and heavy horizontal lines indicate the average value of normalized coating thickness measured between these rebuilds. These significant variations mean that the coating thickness specification window, the range of acceptable variation, would have to be quite large to avoid having to do significant re-work. If the acceptable range for a particular customer was narrower the rework would add costs from wasted spray booth and operator time, wasted powder, and the need to remove excess coating from some of the parts. Since actual production parts are curved, which increases variations, the coating thickness specification window is typically set at +/−20% of the average thickness.

A paper by Gevelber, M. A., C. Cui, B. Vattiat, Z. Fieldman, D. Wroblewski and S. Basu, "Real time control for plasma spray: sensor issues, torch nonlinearities, and control of coating thickness", Proceedings of the 2005 International Thermal Spray Conference, 2005 pp. 667-672 ("the Gevelber paper"), showed that control over certain parameters has the potential to significantly reduce variations in coating thickness. But the results depend on selecting a plume property to control that correlates well with coating thickness.

The experimental data in the Gevelber paper showed that the amount of variation itself varied with the parameter being closed-loop controlled, as shown in FIG. 2. Using an individual particle sensor the authors measured particle temperature and velocity for particles in the plume. They found that control of ensemble averages of particle temperature (labeled Tp) or both temperature and velocity (labeled Tp+Vp) actually led to more variation compared to no control at all (labeled open-loop). In contrast, they found that control of the flux of molten particles in the plume and the plume position (labeled Dep and Yc) showed substantially less variation and reduced the standard deviation of the variation by a factor of 3-5.

Prior art sensors for plasma spray monitoring and control fall into two main categories. (1) Full-plume sensors and (2) Individual particle sensors. Full-plume sensors provide bulk average characteristics of some ensemble of particles in the plume or provide some distribution of one or more quantities across the plume. 2) Individual particle sensors provide temperature, velocity and diameter for each particle passing through a small control volume (typically less then 1 mm$^3$).

Full-plume sensors have not been effective for control because their outputs do not correlate well with coating deposition characteristics, as shown in FIG. 3a, 3b from the Gevelber paper. FIG. 3a is a plot of the average temperature versus normalized cross sectional coating area for those particles observed by a conventional individual particle sensor that was translated to image the entire plume as well as averaged to reflect the output of a full plume sensor. Individual particle temperature measurements were then averaged to reflect the output that a full-plume sensor would have provided. FIG. 3b is a plot of the total intensity observed by a CCD array versus the average coating cross sectional area.

There are four reasons full-plume sensors do not provide effective control: (1) They do not capture the proper volume-weighting of individual particles that characterizes the coating buildup from individual particles since the average is based on the cross sectional area of only those particles that are able to be detected through the limitations of the dynamic range. (2) Since primarily those particles which are molten contribute to the coating, measurements of bulk average quantities are not indicative of the subset of particles which will determine the coating properties. Intensity or bulk temperature will tend to be skewed to larger, cooler particles, as evidenced by the fact that the temperature obtained from bulk sensors is often below the melting point for YSZ sprays. (3) The detectors used in the sensors do not have the dynamic range needed to sense all particles. The dynamic range is the ratio of the largest to smallest intensity signal the sensor can detect, which determines the intensity the sensor can detect at the same time from small hot particles to large cold particles. When the sensors are operated in a configuration that avoids saturation of the detectors by the largest and brightest particles, they may miss a significant number of smaller particles that many times comprise the critical subset of molten particles. In the conventional sensor schemes, the dynamic range requirements are not easily met since it is difficult to observe the light from small particles which contribute to the coating, along with the large intensity observed from cooler, larger particles. (4) Bulk average sensors are unable to detect relative particle position and therefore unable to spatially resolve particle characteristics which affect coating thickness uniformity, and as such they cannot be used to monitor and adjust plume position.

Individual particle sensors are too slow for control, since they need to be able to measure 100,000 to 1,000,000's of particles across the whole plasma plume (10-20 mm). But since conventional individual particle sensors have small measurement volume (less than 1 mm$^3$), measure particles one-by-one, and require translation to measure particles across the whole plume, the measurement of a large number of particles would take a long time. Thus individual particle sensors have not been suitable for robust monitoring and control. In addition, the individual particle sensors are subject to the same limitations in dynamic range to determine the molten particle flux relative to the entire particle flux.

Thus, the individual particle sensor technique of the Gevelber paper has not been suitable for monitoring the state of the particles during production runs. Therefore, a better scheme is needed to monitor the state of the particles, and this scheme is provided in the present patent application.

SUMMARY

One aspect of the present patent application is a method of measuring parameters of a particle. The method includes providing a particle, wherein the particle has a first portion and a second portion. The method also includes providing a column of photo-detectors, including a first photo-detector and a second photo-detector. Light is projected from the particle onto the column of photo-detectors wherein the column of photo-detectors is oriented so the light from the first portion is projected onto the first photo-detector and light from the second portion is projected onto the second photo-detector. The amount of light measured by the first photo-detector differs from amount of light measured by the second photo-detector. The process further includes using the different first and the second photo-detector measurements to determine at least one from the group consisting of particle temperature and particle diameter.

Another aspect of the present patent application is a method of measuring parameters of a particle. The method includes providing a tool for spraying particles and spraying a plurality of particles with said tool. The method also includes providing a column of photo-detectors. Light is projected from the plurality of particles and this projected light is provided to the column of photo-detectors as the particles move away from the tool. Light is then collected with the column of photo-detectors for an interval of time. Particle temperature and particle diameter of each particle of the plurality of particles is determined based on the light collected from the plurality of particles during the interval of time.

Another aspect of the present patent application is a method of measuring parameters of a particle. The method includes providing a particle traveling through a measurement volume, wherein the particle has a first portion and a second portion. The method also includes providing an array of photo-detectors including a first photo-detector and a second photo-detector, wherein the first photo-detector and the second photo-detector are sensitive to the same range of light frequencies. An optical system is provided that collects light from the particle as it travels through the measurement volume and projects the light onto the array of photo-detectors. The optical system projects light from the first portion onto the first photo-detector and light from the second portion onto the second photo-detector. The method includes receiving light from the particle during an interval of time with a plurality of the photo-detectors of the array of photo-detectors. The method also includes using intensity of light as measured by each of the plurality of photo-detectors of the array of photo-detectors to provide intensity of light as a function of position data and determining temperature of the particle from the intensity of light as a function of position data.

BRIEF DESCRIPTION OF THE DRAWINGS

The foregoing will be apparent from the following detailed description as illustrated in the accompanying drawings, in which:

FIG. 7a is a front view schematic drawing showing projected light from a particle moving across the columnar array of photo-detectors and showing that the photo-detector or pixel receiving light from the central region of the particle receives more light than pixels above and below;

FIG. 7b is a schematic intensity profile of the particle crossing the measurement volume of FIG. 7a;

FIG. 8 shows the measured intensity profiles of a large number of particles crossing the measurement volume in an experiment conducted with the PSF of the present patent application;

FIG. 18 is a schematic diagram showing an optical system and a photo-detector array of the present patent application mounted on a torch for optically analyzing a particle plume continuously while the torch scans across a substrate;

FIG. 19a is a schematic diagram showing adjacent red, green and blue columnar photo-detector arrays;

FIGS. 19b-19d are intensity as a function of position for each color of a three color array.

DETAILED DESCRIPTION

The present patent application provides a particle state and flux sensor (PSF) that allows improved control over coating deposition during production runs. The PSF of the present application not only measures particle mass flux, but also can determine which particles are molten. These are the particles entrained in the jet that have a high enough temperature to bond to the target. The PSF can determine the molten particle mass flux, which is the parameter that applicants found correlates best to the mass of the coating that is deposited. The present applicants found that the volumetric flux and mass flux rates of molten particles measured with the PSF corresponds well to deposition rate measured on the substrate. They found that the measurements provided by the PSF allow for adjusting the processing conditions, either manually by the operator or using real time automatic feedback control, to reduce part to part coating variation. Applicants found that use of the PSF to measure volumetric mass flux rate of molten particles allowed for substantially greater control over coating thickness, narrowed the thickness variation, and permitted a substantially lower coating thickness specification window. The particle state measurements also provide a basis for evaluating a particular process.

The PSF performs its measurements at a rate fast enough for a human or computer-based controller to react to disturbances. In use, the sensor measures the state of particles, including the temperature, diameter, location, and velocity of individual particles, and the flux rate of particles that pass through a measurement volume.

The powdered feedstock material may be zirconia, yittria stabilized zirconia, and zirconium oxide. It can also include metal particles or other ceramic particles, such as aluminum oxide, titanium oxide, titanium based alloys, and nickel based alloys, such as NiAl and NiCr.

Besides measuring particles in gas and plasma jets, the sensor of the present patent application can also be used to measure particle state and particle flux rate for processes including High Velocity Oxygen-Fuel (HVOF) and Detonation Gun (DGUN). It can also be used for other particle spray processes such as combustion powder spray and various wire spray techniques, such as an arc sprayer.

Figure 1:
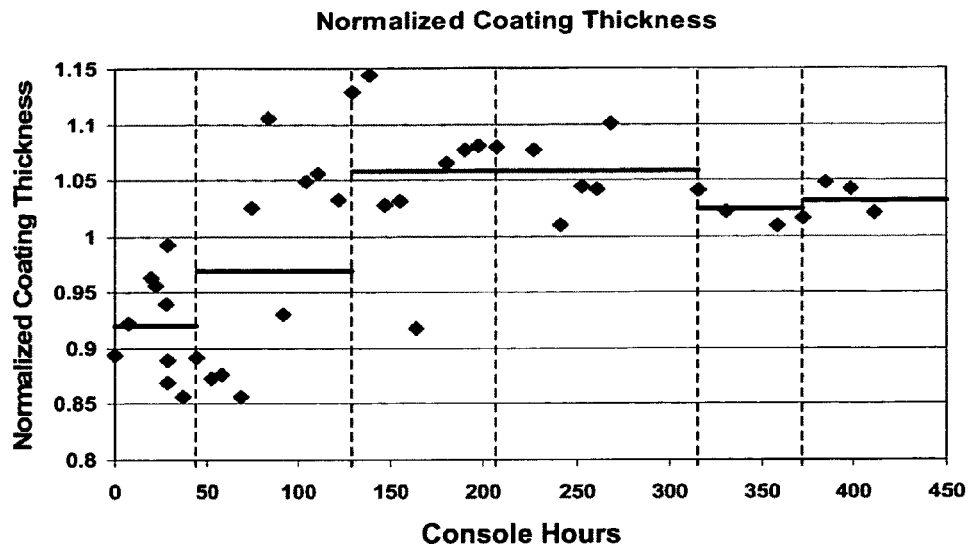
FIG. 1 is a graph showing run to run prior art coating thickness variation during manufacturing production spray deposition.
Figure 2:
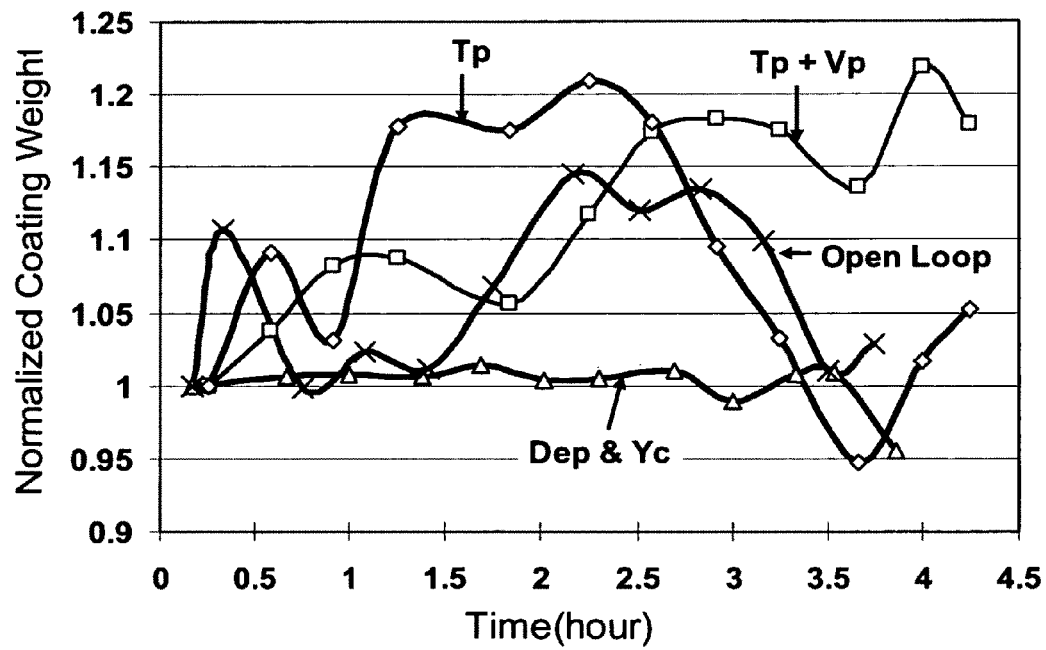
FIG. 2 is a graph showing results of a prior art coating thickness variation experiment comparing control over particle temperature, control over both particle temperature and particle velocity, and control over molten flux rate.
Figure 3A:
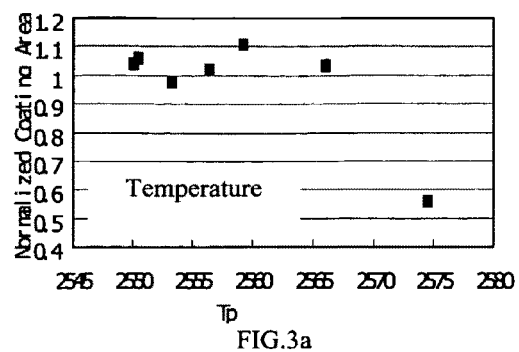
FIG. 3a is a graph showing average temperature versus normalized cross sectional coating area for particles in a plume observed by a conventional individual particle sensor that was translated in steps across the plume to image the entire plume, and the results were averaged to reflect the output of a full plume sensor.
Figure 3B:
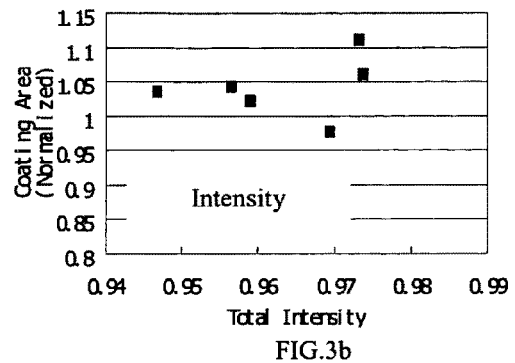
FIG. 3b is a graph showing the total intensity observed by a CCD array versus the average coating cross sectional area.
Figure 4:
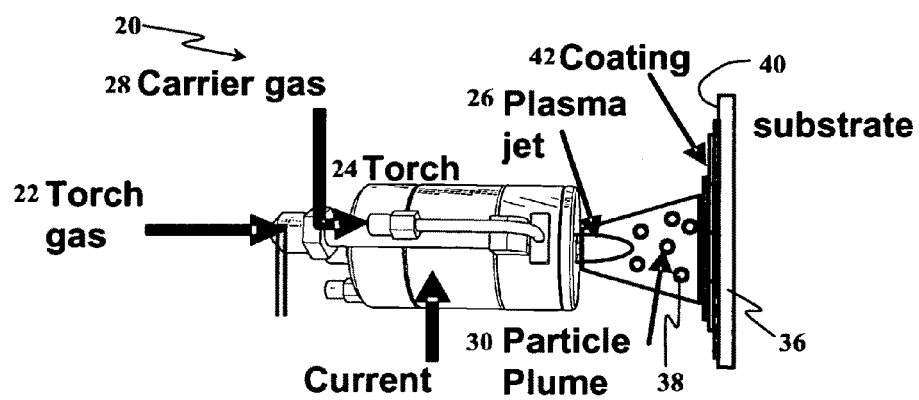
FIG. 4 is a side view of a schematic drawing showing a plasma spray deposition system with torch gas flowing through a torch that provides an electric arc which energizes the gas into a plasma state and ejects it as hot plasma jet and that also has a carrier gas with powdered material that is heated and accelerated in the torch and carried for deposition on a substrate surface.

In plasma spray deposition system 20, gas 22 flows through torch 24 that provides an electric arc which energizes gas 22 into a plasma state and ejects it as hot plasma jet 26, as shown schematically in FIG. 4. Fine powders (10-90 microns for YSZ TBCs), suspended in carrier gas 28, are injected into plasma jet 26, where the particles are accelerated and heated through momentum and thermal interactions with plasma, 26, producing particle-laden plume 30 that is directed at substrate 36. Molten particles 38 in particle-laden plume 30 rapidly flatten and solidify on contact with surface 40 of substrate 36, forming splats that build up to form coating 42 as torch 24, on a robotic arm (not shown), is moved over substrate 36.

The plasma-particle plume 30 is a complex thermal, fluid system with characteristics that depend on the torch inputs, including torch current, gas flow-rates, and powder feed rates, as well as the torch arc. Even with constant torch inputs, significant variations and distributions in particle states (velocity, temperature, and diameter) exist due to inherent spatial gradients and temporal variations of the plasma jet that arise from electrode erosion, arc fluctuations, etc. occurring over a wide range of time scales. These variations, as well as the related variation of particle trajectories through the plume, account for the wide distributions of particle states and the resulting long and short-term variations in coating thickness.

During a production run, an operator may have difficulty detecting when these variations cause the coating to be outside the specifications, and even more difficulty compensating for them by returning the torch to a state where it can deliver that specification.

The complexity of the particle-plume interactions/variations motivate the need for a sensor that can detect properties of the particle plume that directly relate to the critical properties of the coating that is being deposited. To be effective in terms of measuring particle characteristics that relate to the current deposition rate of the torch, the present applicants found that a plasma spray sensor that has the following capabilities is useful:

- The sensor is capable of measuring either particle mass flux or particle volume flux so the sensor can provide information related to the resulting coating mass buildup.
- The sensor can detect those characteristics of molten particles that allow determination of molten mass flux.
- The sensor can image the whole plume fast enough so that the torch can be adjusted during the coating process to reduce thickness variation. The sensor can image the whole plume to take into account variation in particle flux across the plume, variation for different torches, and variation between molten and unmolten particles.
- The sensor has a wide dynamic range for intensity, allowing it to detect the full range of particles in the plume since the emitted particle intensity scales with the square of the particle diameter and the fourth power of the particle temperature.
- The sensor is functional in the harsh environment of a production spray facility.
- The sensor can determine the spatial distribution of the molten flux, which varies over time for a particular torch and which varies from one torch to another.

In addition to providing data for controlling deposition rate, the PSF can also provide information related to coating structure, including porosity, density and crack structure. Density is mainly governed by porosity. Porosity is mainly determined by the flattening process by which molten particles form into splats, and in particular the extent to which splashing and void formation occur. Crack structure is determined by the stresses of splat solidification.

Control over the size and distribution of microcracks and voids helps achieve the necessary compliance, thermal properties and reliability of TBCs.

Particle-surface interactions have been studied to identify factors that affect the stresses during splat solidification that lead to microcrack formation, as described in a paper by Basu S. N., Ye G., Gevelber M., and Wroblewski D., "Microcrack formation in Plasma Sprayed Thermal Barrier Coatings", *International Journal of Refractory Metals and Hard Materials*, 23, 335-343 (2005). Parameters that affect the stresses are the temperature difference between the splat and the substrate and the splat thickness. The temperature difference is related to particle superheat. The splat thickness is determined by the size, velocity and temperature of the molten particle.

Figure 5:
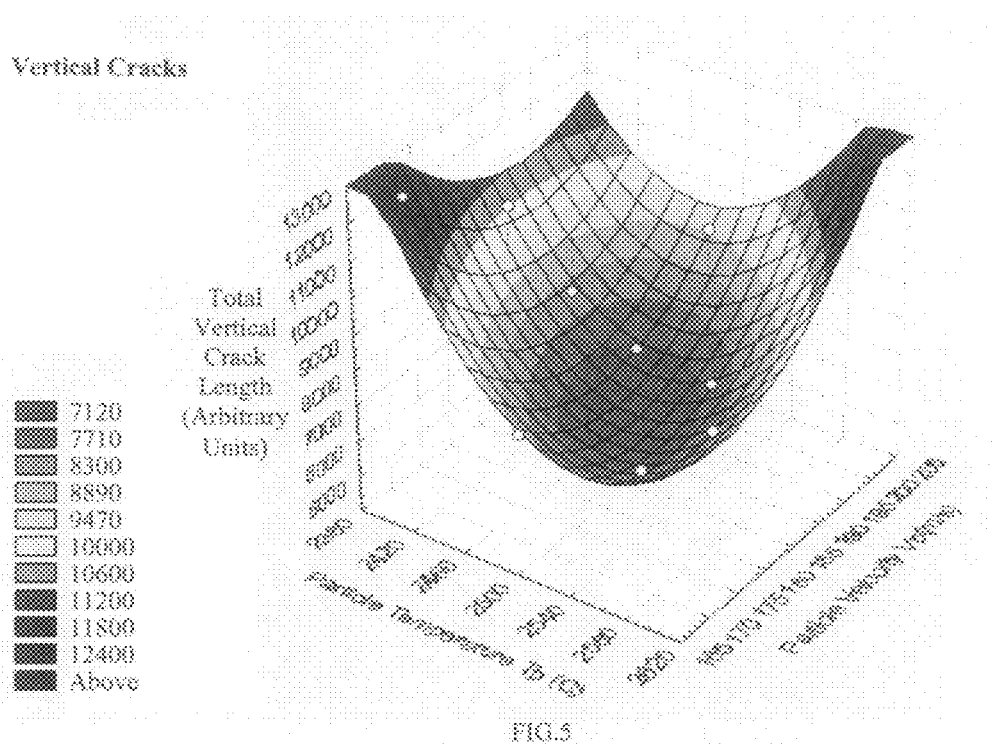
FIG. 5 is a graph showing the distribution of total vertical crack length as a function of average particle superheat temperature and particle velocity.

A plot of the distribution of total vertical crack length as a function of average particle superheat temperature and particle velocity, shown in FIG. 5, illustrates an example of the effect of these parameters on measured vertical crack length of sample coatings.

In addition to measuring the particle flux rate, the PSF of the present patent application can also measure the temperatures and velocities of just the molten particles which gives information related to these crack related coating properties. Such an integrated sensor thus provides all the measurements that may be needed to control the thickness, density and microstructure of a coating.

Figure 6A:
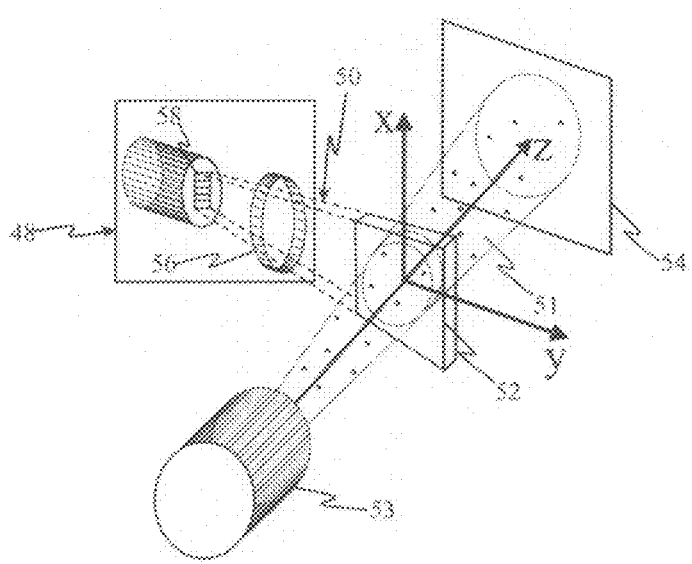
FIG. 6a is a three dimensional schematic drawing showing a plasma spray deposition system spraying a plume of particles toward a substrate and showing a columnar photo-detector array receiving light projected by an optical system from a measurement volume of the plume, and showing that the optical system has a large enough depth of field that the measurement volume extends substantially across the entire plume.
Figure 6B:
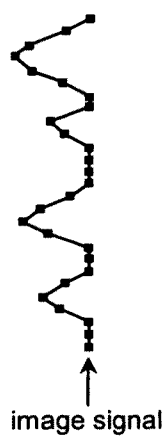
FIG. 6b is a front view of an array of photodiodes that has fine enough resolution so that the projection of each moving particle traveling through the measurement volume illuminates multiple neighboring photo-detectors, providing a spatially resolved intensity versus position profile for each during the exposure time.

PSF 48 captures a spatially resolved snapshot of light 50 emitted by particles in plume 51 passing through measurement volume 52 during an exposure time, as shown in FIG. 6a. Measurement volume 52 has a length that extends normal to the direction particles primarily move along axis z of torch 53 toward substrate 54. Light 50 from measurement volume 52 is directed by optical system 56 to columnar array of photo-detectors 58. Measurement volume 52 is the area in plume 51 that optical system 56 focuses and projects onto columnar array 58. Measurement volume 52 has a width along the Z axis that is determined by the width of columnar array 58 and by the magnification provided by optical system 56. The X axis is chosen to be perpendicular to the Z axis, and aligned with the length of the array 58. Measurement volume 52 has a length along the X axis that is determined by the length of columnar array 58 and by the magnification provided by optical system 56. The measurement volume images particles in focus along the Y axis that is determined by the depth of focus determined by optical system 56. The Z axis is along the torch center line, and particles have a dominant path of motion along the Z axis. The Y axis is perpendicular to both the Z and X axis.

Columnar array of photo-detectors 58 provides both the magnitude and spatial distribution of the light intensity. Intensity of light at each photo-detector of columnar array 58 is determined by the particle's characteristic states, including particle diameter, temperature, and velocity. A computer implemented algorithm, described herein below, analyzes the intensity distribution across array 58 to determine particle diameter and temperature of particles passing through measurement volume 52 during the exposure time. Because measurement volume 52 observed by columnar array 58 extends across plume 51 the algorithm can also determine the number flux rate, which is the number of particles per unit area per unit time.

Figure 6C:
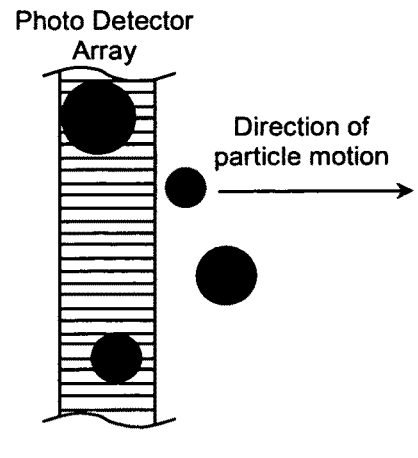
FIG. 6c is a schematic intensity profile of the particles crossing the measurement volume of FIG. 6b.

In one embodiment, optical system 56 focuses light from measurement volume 52 spanning torch plume 51 onto columnar array 58 of photo-detectors, as shown in FIGS. 6a-6d and 7a. An array that includes 2048 photodiodes has fine enough resolution so that each moving particle 70 traveling through measurement volume 52 will provide light that is projected by optical system 56 to illuminate multiple neighboring photo-detectors or pixels 72m, 72n, 72o, 72p, 72q of array 58, as shown in FIG. 7a and FIGS. 6b-6d. A spatially resolved intensity profile for a single particle, as shown in FIG. 7b, and for multiple particles, as shown in FIG. 6c provides a distinct intensity as a function of position profile for each particle flowing through the measurement volume during the exposure time. Characteristics of moving particle 70, including particle diameter and particle temperature, can be determined from these profiles. By adjusting the photo-detector exposure time such that peaks recorded are well-defined and not overlapping, the peaks may be accurately counted and analyzed by a simple computer algorithm described herein below to also provide the particle number flux rate.

Optical system 56 may be a lens such as a Radogon 80 mm lens, with F4-22 aperture, available from Linos located in Gottigen, Germany. Photo-detectors 72m-72q may be neighboring pixels of a solid state photo-detector, such as the 2048 pixel linear array (LW-SLIS-2048A) available from the Imaging Solutions Group (ISG) located in Fariport, N.Y.

Different pixels 72m, 72n, 72o, 72p, 72q of array 58 receive different intensity levels during the exposure time depending on the temperature, size, and speed of particle 70. The particle's movement and the corresponding movement of its projected image across array columnar array 58 during the exposure time provides the intensity as a function of position profile of FIGS. 7b and 6c.

By using a photo-detector array that includes a large number of photodector pixels it is possible to detect and measure many particles in a single exposure. One embodiment uses a commercially available CMOS array of 2048 photo-detectors with 12 bit resolution, such as an ISG camera having part number LW-SLIS-2048A. This array has 7 by 7 micron size pixels and has a 14.3 mm by 7 micron sensing area that is 2048 pixels long and 1 pixel wide. A variety of different array lengths and pixel sizes may be used for the PSF. The longer the array and the smaller the pixel size, the smaller the particle that can be resolved for while still measuring the whole plume at one time. Basler located in Ahrensburg Germany, makes a family of different linear array cameras 1024, 2098, 4080, and 8160 pixels in length, with pixel dimensions of 14, 10 and 5 microns.

Figure 6D:
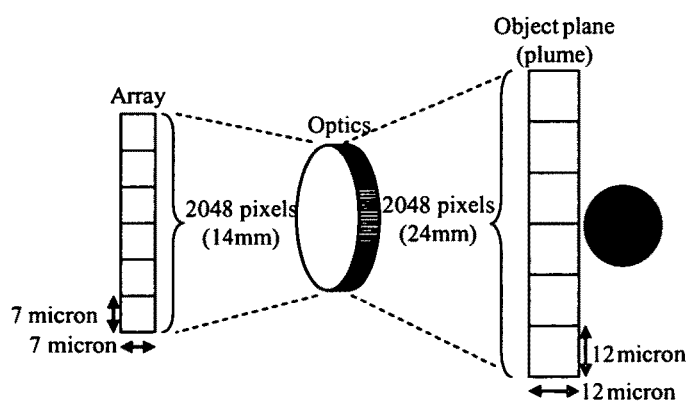
FIG. 6d is a three dimensional schematic drawing showing the relation between the dimensions in the plume and the dimensions of the image projected on the sensor array by the optical system for an optical system with a magnification.

Using an optical system with primary magnification of 2.0 would result in a measurement volume having an area 14 mm wide by 24 mm tall. The measurement volume is defined by the area of columnar array 58 and by the magnification of optical system 56. The relation between the particles in the plume and the image projected on the sensor array by the optical system is illustrated in FIG. 6d. For the system used to collect data shown in FIG. 10, a Rodagon large format Linos 180 mm lens, with F4-22 aperture was used. The measurement area defined by the CMOS array and this lens spanned the range of trajectories for all particles in the torch plume. Other optical systems can be used. Considerations in choosing an optical system include the size of the plume area to be imaged and the depth of focus so that the majority of particles imaged by the array are in focus and their size is not distorted. One option is to change the focus of the optical system so that it is centered about the line of greatest particle flux (or molten particle flux), and select a depth of focus by varying the aperture to capture 80 to 90% of the particles.

Exposure time of the ISG 2048 linear CMOS array is adjustable from 701 is to 2.2 ms. Applicant found that 7011 s provided good results for the process conditions used in testing. Shorter exposure times reduce the number of particles imaged per frame, reducing the possibility of overlapping particles on the photo-detector array. Multiple particles are still exposed in one frame since typically, the whole plume is imaged. For example, for a 10 micron pixel, the time the particle projects onto the array for a 40 micron particle traveling at 100 m/s is 0.5 μs. Thus, given that the shortest exposure time is on the order of 5 μs, and that the whole plume has particle flux rates of hundreds of thousands to millions of particles per second, there is a good probability that multiple particles will be imaged in one exposure by different parts of the array. However, there is also a choice of sampling rates in commercial cameras, such as the Bassler linear array cameras that have 7200, 9400, and 14,100 frames per second, which provide the designer with a range of options. The exposure time is less than the inverse of the frame rate so these linear array cameras can have an exposure time less than 138 to 7111 s.

Temperature and diameter of particles can be determined from the intensity data collected by array 72. One embodiment uses the fact that intensity is proportional to the fourth power of particle temperature and is also proportional to square of the particle diameter. For a particle having a diameter larger than the width of the measurement volume, the length of time the particle takes to pass through the measurement volume corresponds to the particle diameter, as shown in FIG. 7a. For spherical particles, the second spacial derivative of the intensity with position is proportional to the fourth power of temperature and inversely proportional to particle diameter. These two measurable parameters at the peak can be used to determine the temperature and diameter of a particle, as further described herein below.

In another embodiment, an ellipse can be fit to the intensity as a function of intensity as a function of position data around the peak, and the unknown temperature and particle diameter can be calculated. This method is implemented by decoupling the diameter calculation from the temperature calculation.

In general, the PSF calculates particle characteristics based on the spatial distribution of measured intensity. Thus, different parts of the particle are imaged by different parts of the array, and this results in a reduction of the required sensitivity as compared with prior art methods in which a photo-detector received light from all parts of the particle. This reduction is reflected in both of the embodiments described above since they both use either the spatial gradient information which uses data from neighboring pixels, or fits an ellipse to actual intensity measured at multiple pixels.

Dynamic range requirements of the sensor of the present patent application can be substantially less than dynamic range of a prior art single particle sensor. The prior art single particle sensor must have a dynamic range that spans the full intensity of emitted light for a broad range of particle conditions that typically occur in a torch jet (i.e. ranges of particle temperature and diameter). The required range is large for most applications since the emitted intensity is proportional to the particle surface area, which goes as the square of the particle diameter and to the forth power of the particle temperature, since in the conventional scheme, these measurements are coupled.

In the PSF scheme of the present patent application, the intensity from large particles is spread among several detectors of the array so each photo-detector is less susceptible to sensor saturation. In addition, while the intensity for conventional single particle sensors is proportional to the surface area of the particle, or to the diameter squared, for the PSF sensor it is proportional only to the diameter to the first power. Both of these effects lead to a significant increase in the range of detected particle size and temperature for the PSF scheme for a given detector dynamic range. Another advantage is that the diameter and temperature measurements can be decoupled from each other, thus reducing the required sensitivity.

Figure 9:
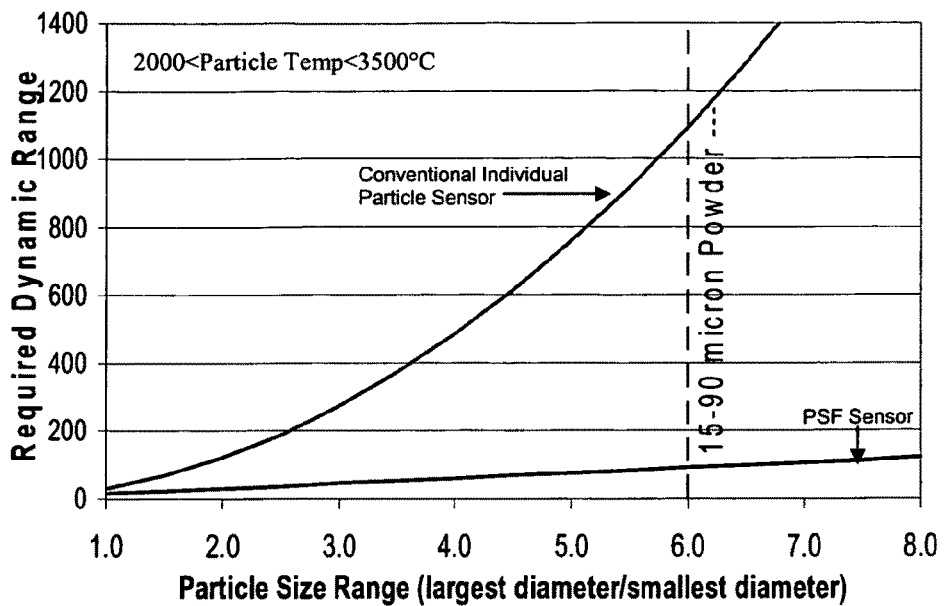
FIG. 9 is a graph showing the dynamic range needed for both conventional individual particle sensors and for the PSF of the present patent application.

Comparison of required dynamic range in FIG. 9 illustrates this effect, showing the required dynamic range for particles in the 2000 C to 3500 C range for different particle size range ratios, for both conventional individual particle sensors and the PSF of the present patent application. For powder ranging in size from 15 to 90 μm a conventional individual particle sensor requires a dynamic range that is more than 1000 times that required by the PSF.

Figure 10:
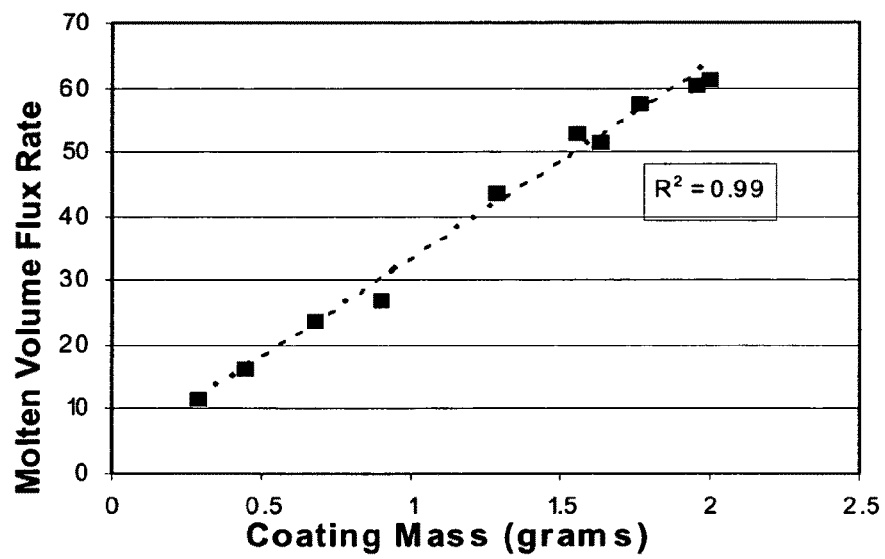
FIG. 10 is a graph showing experimental data demonstrating that coating mass on the substrate tracks well with molten volume flux rate as measured by the PSF of the present patent application.

The PFS scheme was implemented using a 2048 linear array of photo-detectors, and the performance was evaluated by varying the plasma torch operating conditions in a manner to produce variations in the deposition rate. At each torch condition, flat substrates were sprayed with a fixed raster pattern. The substrates were weighed before and after deposition, and these weights were compared to the sensor outputs obtained just before the substrates were sprayed. For the test, the powder feed rate was held constant and the torch inputs, including current, torch gas flow and the carrier gas flow for a SG 100 torch, were varied. Varying torch inputs altered the plasma jet conditions, changing the distribution of molten and non-molten particles. As seen in FIG. 10, molten volume flux rate measured by the PFS correlates well with coating mass deposited on the test substrates for the different input conditions used in the experiment.

The molten volume flux for the experiment was calculated from the intensity profiles measured by photo-detectors of the array, as shown in FIG. 8 for one sampling period for only a portion of the full array. Each peak in the intensity profiles of FIG. 8 represents one particle crossing the measurement volume. The detected peaks are marked by a diamond and the intensity for each pixel is represented by a square.

The data of FIG. 8 was obtained with the ISG 2048 linear array, operating with a 70 μs exposure time. The experiment was conducted with an SG 100 torch, spraying YSZ 10-75 micron powder. Under these conditions, an average of 50 particles were observed for each sample. The optics were selected to have a depth of field sufficient to image the entire plume along the x direction. A 5.6 aperture was used to capture 90% of the particle volume flux of the particular spray conditions, centered about the intensity centroid. Under these conditions, the sensor deterected a particle flux rate of 710,000 particles per second.

The experiment demonstrated that the PSF:
- can measure the diameter, temperature and position of particles across the entire plume without physically moving the sensor.
- can filter out non-molten particles that don=t contribute to the coating.
- has a greater dynamic range for sensing individual particles due to its multi-detector architecture.
- is fast enough for closed loop control.

While the number of particles counted during the photo-detector exposure time provides information as to the number of particles in the plume, it does not necessarily determine the number of particles in the plume that are above the particle melting temperature and that can therefore contribute to the coating. Furthermore, simply counting the particles does not account for that fact that larger particles will contribute more to the coating than smaller particles. The PSF obtains this information by determining each individual particle=s temperature and size from the details of the observed peaks. In addition, averaging metrics based on weighting factors can be used to characterize the plume as a whole. Characteristics of sub-distributions of the plume, such as particles having a temperature above (or below) a specified threshold can be determined, and analysis of such a sub-distribution enables the PSF to better calculate quantities that correlate well to deposition rate.

Figure 11:
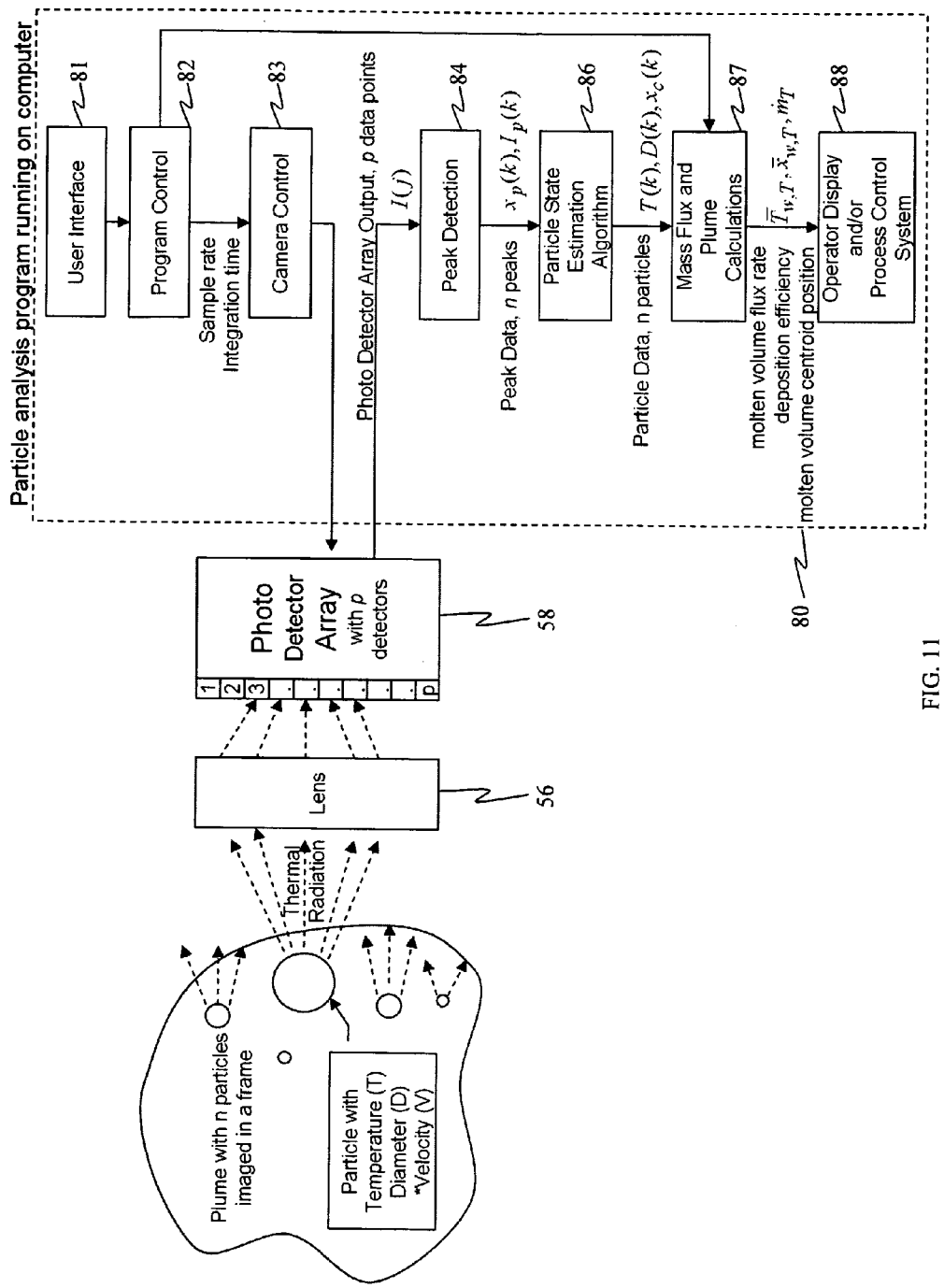
FIG. 11 is a block diagram of the apparatus and a flow chart showing the program implemented on a computer that analyzes the data from the photo-detector array to provide individual particle temperature and diameter and to calculate aggregated variables such as molten mass flux and centroid position of all the particles or of molten particles in the plume.

Program 80 implemented on computer 82, as shown in FIG. 11, analyzes the data from photo-detector array 58 to provide individual particle temperature and diameter and to calculate aggregated variables such as molten mass flux and centroid position of all the particles or of molten particles. The program can also provide feedback to adjust parameters of torch 53.

Program 80 running on computer 82 includes a user interface 81 and program control 82, camera control 83 to the photo-dector array, and implementation of the algorithm to determine particle states and flux. The algorithm includes detection of the peak intensities in box 84 for each observed particle, the estimation of particle states in box 86 such as temperature, diameter, and location, and the calculations of plume characteristics in box 87 such as molten volume flux, centroid position, and averaged state property values such as average temperature, position, etc. The algorithm allows calculation of these averages for relevant subdistributions, such as for those particles over a certain temperature, size, or velocity. The PSF system also has an output module 88 to provide information to the operator, or to provide data for real time automatic control of torch 53.

The temperature and diameter of particle 70 are estimated by measuring the intensity of pixels around peak 84 of the intensity profile, as shown in FIG. 7b. Several methods can be used to determine the corresponding particle temperature and size from this data including a) using the peak and second derivative, and b) obtaining a best fit to an elliptical function.

One method uses the intensity and second spatial derivative of intensity at each peak. Both are proportional to intensity of light emitted by a particle and the length of time that particle is illuminating the photo-detector array. The intensity of light emitted by the particle is proportional to the forth power of the particle temperature. The length of time the particle illuminates the photo-detector array is proportional to the diameter of the particle. Therefore:

$$I_p \approx T^4 * D \quad \text{(eqn. 1)}$$

where:

$I_p$ is equal to the measured peak intensity.

D is the particle diameter,

T is the particle temperature

The second spatial derivative of a peak is also related to the temperature and diameter of the particle when the particle is viewed as a disk and recalling that the magnitude of light measured by each photo-detector is proportional to the length of time that photo-detector is illuminated. Since the particles are bigger than the measurement area defined by a single photo-detector, a single particle will illuminate multiple photo-detectors. The photo-detector which is illuminated by the center chord of the particle will be illuminated for the longest period of time compared to those adjacent photo-detectors, which are illuminated by the edges of the particle. Therefore the photo-detector illuminated by the center chord of the particle will record a larger intensity signal. This concept is illustrated in FIG. 7a, 7b.

The intensity measured by a single photo-detector is therefore related to the diameter of the particle and the distance that specific photo-detector is from the center chord of the particle:

$$\text{intensity} \approx \text{chord length} * T^4 = 2\left(\frac{D^2}{4} - x^2\right)^{\frac{1}{2}} * T^4 \quad \text{(eqn. 2)}$$

where:

x is the distance from the center chord of the particle

D is the particle diameter,

T is the temperature of the particle

Taking the second derivative of the equation above with respect to x and evaluated at the peak (where x=0) yields:

$$\ddot{I}_{x=0} = \frac{-4}{D} * T^4 \qquad \text{(eqn. 3)}$$

where: $\ddot{I}_{x=0}$ is the second derivative evaluated at the peak

By rearranging equations 1 and 3, the particle temperature and diameter can be determined:

$$T = (I_p * \ddot{I}_{x=0})^{1/8}$$

$$D = (I_p / \ddot{I}_{x=0})^{1/2} \qquad \text{(eqn. 4)}$$

Figure 12:
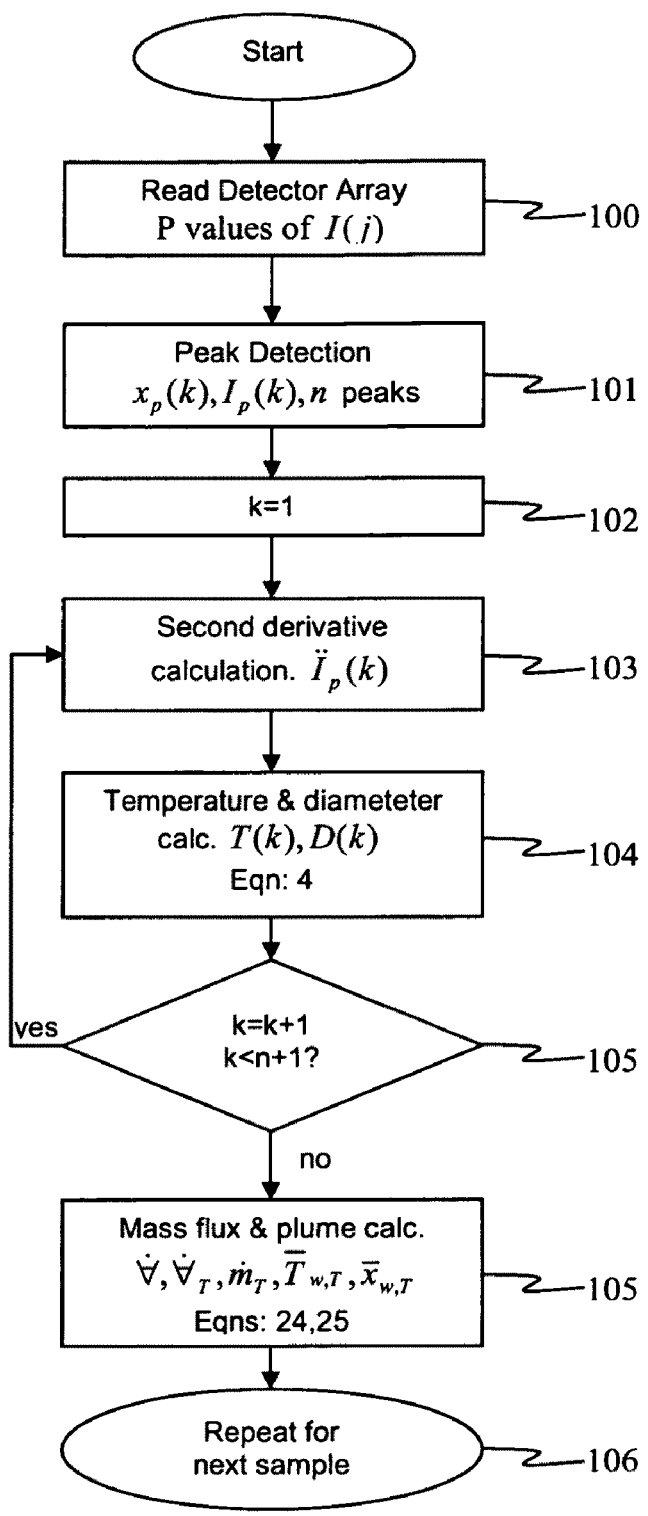
FIG. 12 is a flow chart for a computer program to use the intensity profile at the peak and its second derivative at the peak to determine particle temperature, particle diameter, and parameters of the plume of particles, including mass flux rate.

The peak intensity $I_p$ and the second derivative at the peak ($\ddot{I}_{x=0}$) can both be determined by standard commercial software packages such as National Instruments LabView Signal Processing Toolkit. This algorithm to obtain a measurement for each particle's temperature and diameter, by evaluating eqn. 4, can be implemented in a computer program having a flow chart illustrated in FIG. 12. The program starts by reading data from all the photo-detectors in array 58 during the time interval, as shown in box 100. P is the number of photo-detectors in columnar array 58, i.e. the number of pixels. That array has an index j which corresponds to 1 through P pixels. Then the program determines the number of peaks n that are observed in that frame, as well as the location and magnitude of each peak, as shown in box 101. The second spacial derivative is calculated for each of the peaks, as shown in boxes 102, 103, and the corresponding temperatures and diameters of each of the n particles are then calculated, as shown in box 104. This is repeated for each peak, as shown in box 105. The mass flux, centroid position, and other characteristics of the particles and plume are calculated, per equations 24 and 25, as shown in box 105. The process is repeated for the next time interval, as shown in box 106.

Another method is to estimate the diameter, D, in equation 1, by counting the number of pixels in the breadth of the peak. Then equation 1 is used to solve for T. Since D is estimated from the breadth and $I_p$ is measured as the magnitude of the peak, the temperature can be determined. One way to approximate the breadth of the peak is to measure the peak's width at half maximum amplitude (FWHM). In this approach, the diameter measurement is decoupled from the temperature measurement. This approach is limited however, if the particles overlap, and a distinct and complete peak is not observable.

Another way to analyze the intensity data is determined by analyzing each of the peaks identified in the signal from a single scan of a particle on the intensity sensor array.

Figure 13A:
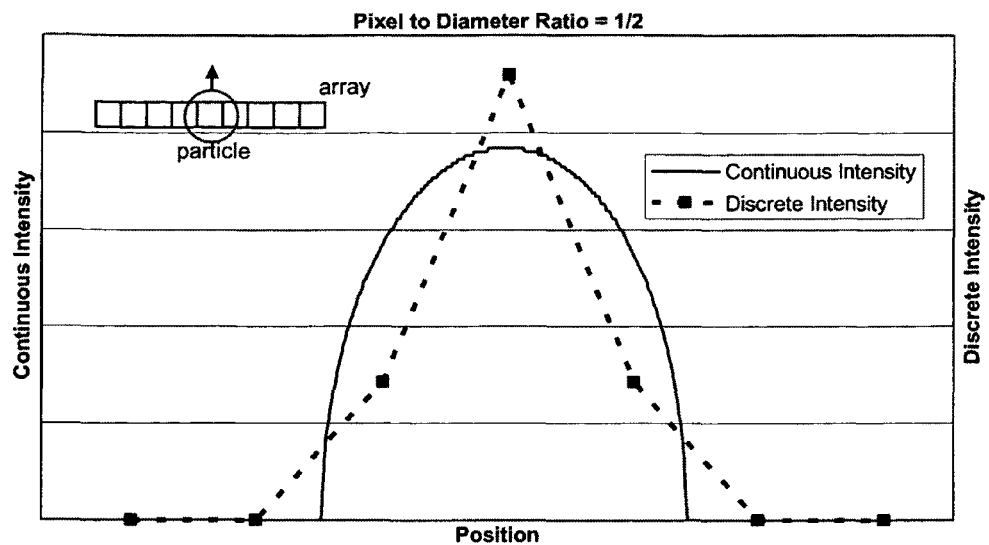
FIGS. 13a and 13b are graphs illustrating intensity as a function of position as measured in a discrete and continuous fashion for two different size particles.
Figure 13B:
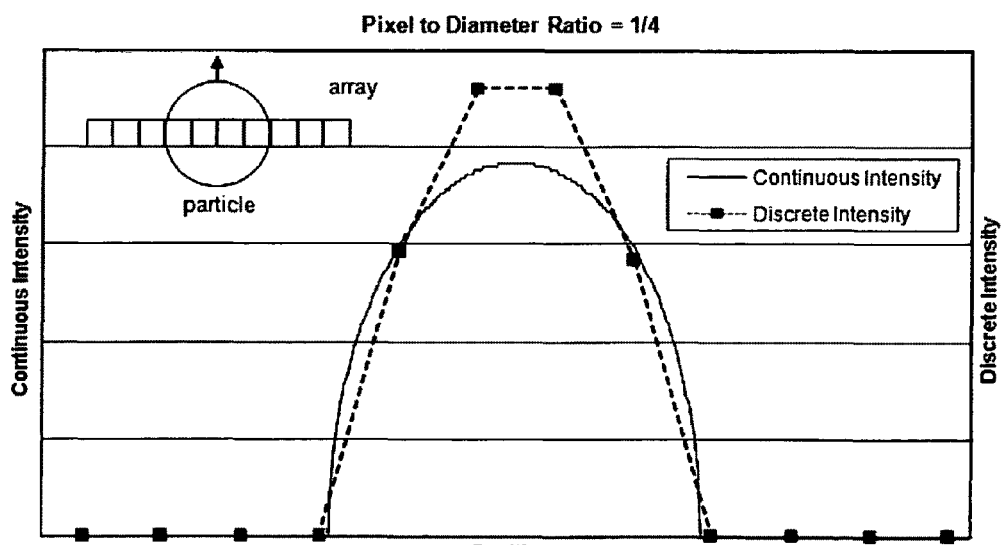

Initially, consider a case in which the intensity I(x), is known as a continuous function of position, corresponding to the idealized case in which the pixel size is much smaller then the diameter of the particle. The relation of the measured intensity in a discrete and continuous fashion is illustrated in FIGS. 13a and 13b for two different size particles. FIG. 13a shows a particle that is 2 pixels in diameter, although it exposes 3 pixels. The graphs of the continuous and the discrete intensity show the differences due to the fact that the particle diameter is close to the pixel size, illustrating the resolution limitations. FIG. 13b shows how the discrete measurement more closely matches the continuous distribution when the particle diameter is 4 times the pixel size. If the particle as at a higher temperature, but of the same size, all measured intensities would be higher, although the distributions would have the same width.

The intensity at a point x observed on the intensity sensor is related to temperature and diameter through the relation $$I(x) = 2C_1 T^4 \sqrt{R^2 - (x - x_c)^2} \qquad \text{(eqn. 5)}$$

where T is the temperature of the particle, $C_1$ is a constant (that includes several radiation-related parameters as well as a factor to account for the camera sensitivity and particle velocity, v), x, is the location of the center of the particle, and R is the radius of the particle. The term $$2\sqrt{R^2 - (x - x_c)^2}$$

is the projected area of the particle that a differential area of the continuous "sensor" is exposed to. Since the curve is continuous, x, can be found by locating the peak in the intensity curve. This maximum intensity value, given by $I_{MAX} = 2C_1 T^4 R$, can be used to normalize the intensity equation $$\tilde{I}(x) = I(x)/I_{MAX} = \sqrt{1 - (x - x_c)^2 / R^2} \qquad \text{(eqn. 6)}$$

This normalization separates the temperature effect from the diameter, facilitating the implementation of the calculation of particle states by decoupling the calculations. Specifically, the normalized equation can be rearranged to $$x = x_c + R\sqrt{1 - \tilde{I}(x)^2} \qquad \text{(eqn. 7)}$$

This is a linear relation between $$\sqrt{1 - \tilde{I}(x)^2}$$

and x so a simple linear regression will provide the slope R. Once R is known, T can be found from $$I(x) = C_1 T^4 \sqrt{R^2 - (x - x_c)^2} \qquad \text{(eqn. 8)}$$

which is a linear relation between I(x) and $$\sqrt{R^2 - (x - x_c)^2} .$$

So a linear regression using these two variables will yield the slope, $C_1 T^4$, providing a measure of temperature to within a constant $C_1^{1/4}$. Note, part of this constant, $C_1$ depends on the velocity of the particle, which will be addressed later in this section. This constant can be determined by the calibration procedure described later in this document.

Figure 14A:
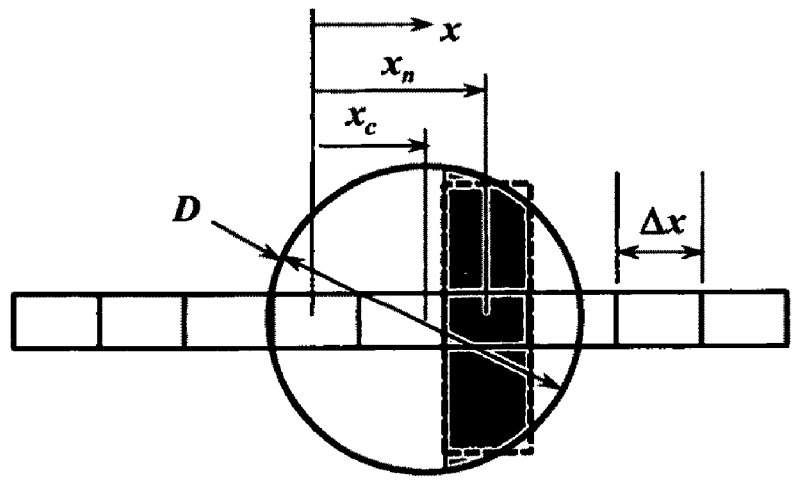
FIG. 14a is a schematic diagram showing the projection of the particle on the columnar photo-detector array, showing the variation of light received by each pixel depending on position, and showing an approximation of this function.

In practice, the intensity is measured as a discrete function by an array of pixels, with the sensor output given by $$I(j)\Delta x = C_1 T^4 A_j \qquad \text{(eqn. 9)}$$

where $A_j$ is the projected area of the particle that the j^th pixel of width $\Delta x$ is exposed to, the gray area shown in FIG. 14a. Note that the intensity I(j) is found from dividing the pixel output by $\Delta x$, the width of each pixel. Note, there are n peaks, and the area of peaks is indexed by k, but the following algorithm is based on obtaining data directly for the pixel array, but about each of the n peaks.

Figure 14B:
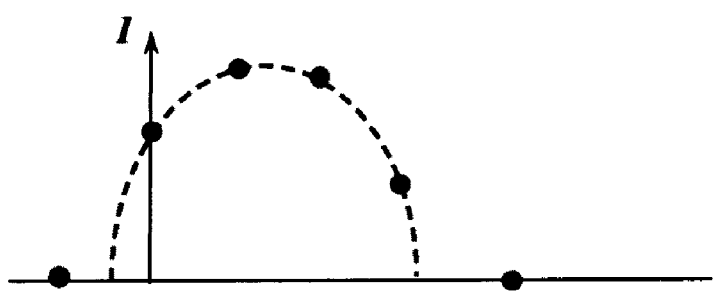
FIG. 14b shows the values of intensity associated with each pixel and the corresponding continuous variation of intensity as a function of position.

$A_j$ can be expressed as $$A_j = \int_{x_n-\Delta x}^{x_n+\Delta x} \sqrt{R^2 - (x-x_c)^2}\, dx \quad \text{(eqn. 10)}$$

where $x_j$ is the location of the center of the pixel, relative to a pixel reference frame, $x_c$ is the location of the center of the particle, $\Delta x$ is the width of a pixel and D is the diameter of the particle. FIG. 14b shows the values of intensity associated with each pixel (data points) and the corresponding continuous curve (dashed line).

The integral for $A_j$ has a closed form solution, $$A_j = c\int_{xj-\Delta x/d}^{xj+\Delta x/d} \sqrt{R^2-(x-x_c^2)^2}\, dx = \quad \text{(eqn. 11)}$$

$$\frac{c}{2}\left\{(x_j+\Delta x/2-x_c)\sqrt{R^2-(x_j+\Delta x/2-x_c)^2} + R^2\arctan\left[\frac{(x_j+\Delta x/2-x_c)}{\sqrt{R^2-(x_j+\Delta x/2-x_c)^2}}\right] - (x_n-\Delta x/2-x_c)\sqrt{R^2-(x_j-\Delta x/2-x_c)^2} - R^2\arctan\left[\frac{(x_j-\Delta x/2-x_c)}{\sqrt{R^2-(x_j-\Delta x/2-x_c)^2}}\right]\right\}$$

While it is possible to develop an algorithm for data analysis using this equation, approximating the integral provide a simpler and faster algorithm.

Several approximations are possible. The following algorithm is just one possibility and can be implemented in a computer program to determine each particles diameter and then temperature:

1. Using the approximation $$A_j \approx \Delta x\sqrt{R^2-(x_j-x_c)^2} \quad \text{(eqn. 12)}$$

which is the area shown in FIG. 14b by the dotted line rectangle. If $D \gg \Delta x$, then this reduces to the continuous relation for the area.

2. The equation for intensity at the jth pixel is then given by:

$$I_j = 2C_1T^4\sqrt{R^2-(x_j-x_c)^2} \quad \text{(eqn. 13)}$$

3. Since the center of the particle will not always be at the center of a pixel, $x_c$ is found by fitting the highest value of $I_j$ and its two neighboring values to a generic quadratic fit $$I(j)=\alpha x_j^2+bx_j+c \quad \text{(eqn. 14)}$$

in terms of a, b, and c, and then solving for x, such that I(j) is a maximum (where one can take the derivative of I(j) with respect to x, obtaining and solving 2 a x+b=0 for the value of $x_c$. This equation is then used to find the true peak intensity $$I_{MAX}=\alpha x_c^2+bx_c+c \quad \text{(eqn. 15)}$$

4. Like the continuous case, the maximum value of the intensity is $I_{MAX}=2C_1T^4R$, and can also used to normalize the intensity equation $$\tilde{I}_j = I_j/I_{MAX} = \sqrt{1-(x_j-x_c)^2/R^2} \quad \text{(eqn. 16)}$$

This can be rearranged to give $$x_j = x_c + R\sqrt{1-\tilde{I}(j)^2} \quad \text{(eqn. 17)}$$

5. The above equation is a linear relation between $$\sqrt{1-\tilde{I}(j)^2}$$

and $x_j$, so a simple linear regression with several data points will provide the slope R and intercept $x_c$, with the normalized intensities found using the peak intensity approximation.

6. With R and $x_c$ known, a linear regression can be performed using I(j) and $$\sqrt{R^2-(x_n-x_c)^2}.$$

The slope will be $C_1T^4$, providing a measure of temperature to within a constant $C_1^{1/4}$. The constant $C_1$ can be determined by calibration procedure described herein below.

7. Since $x_c$ was initially estimated using a generic polynomial, steps 3 through 4 can be repeated to improve the accuracy using the value of $x_c$ and R found from step 5. This iteration can be controlled by checking the magnitude of change in the R calculation ($\delta R$) and $x_c(\delta x_c)$, in relation to the desired tolerances ($L_R$ and $L_x$).

With this iteration, the peak intensity is found from $$I_{MAX}=2C_1T^4R \quad \text{(eqn. 18)}$$

with values of R, and $C_1T^4$ from steps 5 and 6.

Figure 15:
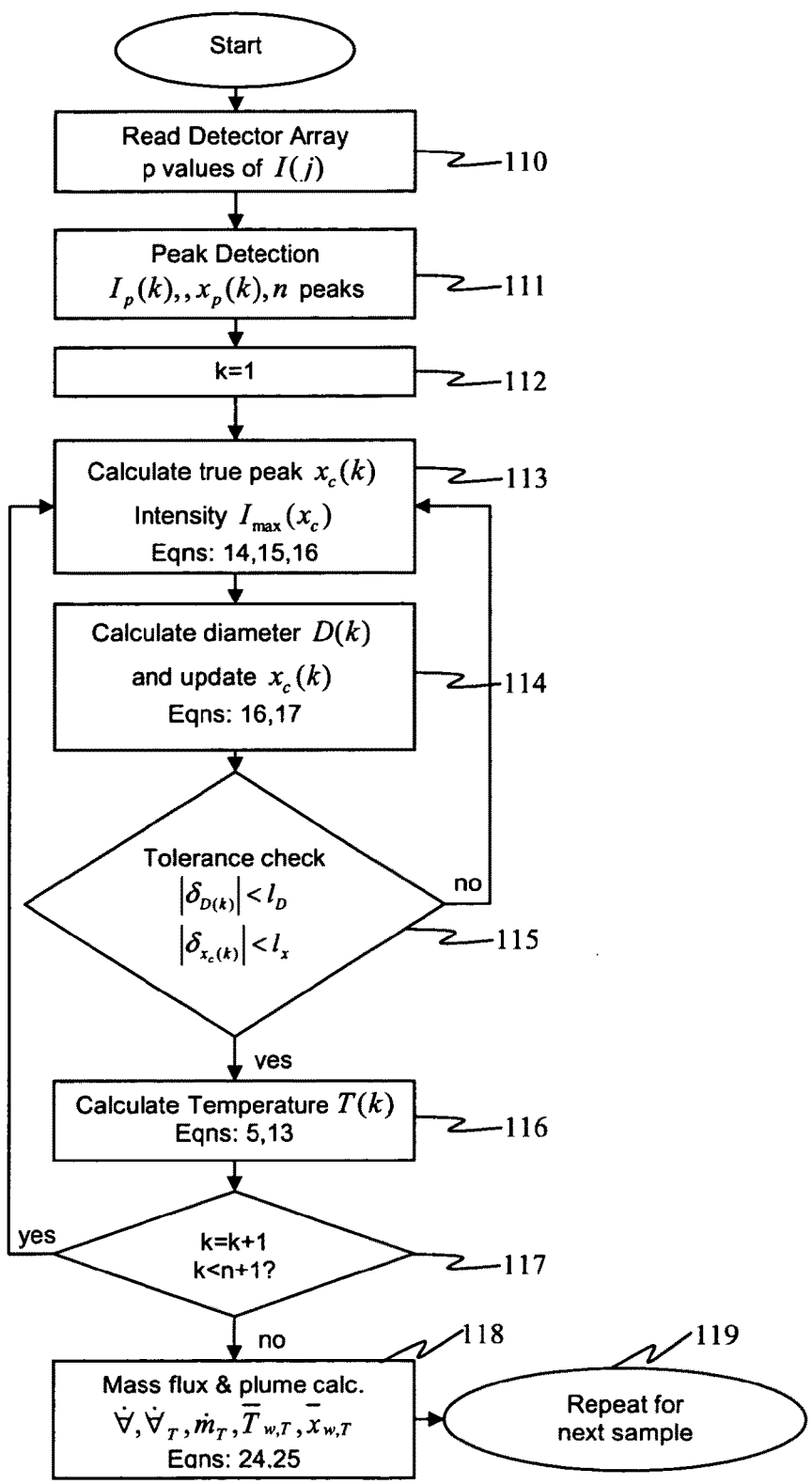
FIG. 15 is a flow chart for a computer program to use the projected area of the particle, which for a spherical particle is an ellipse, to determine particle temperature, particle diameter, and parameters of the plume of particles, including mass flux rate.

The algorithm is illustrated in FIG. 15. The program starts by reading data from all the photo-detectors in array 58 during the time interval, as shown in box 110. P is the number of photo-detectors in columnar array 58, i.e. the number of pixels. That array has an index j which corresponds to 1 through P pixels. Then the program determines the number of peaks n that are observed in that frame, as well as the location and magnitude of each peak, as shown in box 111. The algorithm is applied to all n peaks to measure the diameter, peak location, and particle temperature, controlled by boxes 112 and 117. Box 113 determines both the location of the peak and the peak intensity, utilizing eqns. 14-17. The corresponding particle diameter and temperature are determined in box 114 based on eqns. 16 and 17. The value of the peak location is updated in box 114, and the changes in both peak location and diameter are compared to tolerances in box 115, to determine if further iteration is required. If the diameter is acceptable, then the temperature is calculated in box 116, using equations 5 and 13. The mass flux, centroid position, and other characteristics of the particles and plume are calculated, per equations 24 and 25, as shown in box 118. The process is repeated for the next time interval, as shown in box 119.

This approach can be adopted for non-spherical particles by substituting an appropriate relation for $A_j$ related to the shape and orientation of the particle imaged relative to the array. Thus, instead of using the projected equation based on a sphere (eqn. 10), the more general relation to be evaluated is $$A_j = \int_0^{x_o} y(x)dx \qquad \text{(eqn 10')}$$

where y(x) is the expression relating the boundary of the object expressed in the y direction as a function of different positions in the x direction, out to the objects x direction boundary $x_o$.

In some cases, the absorptivity of the particles is such that the optical depth is very large relative to the particle diameter. In these cases, the intensity emitted by the particle scales not with the square of the radius, but of the cube of the radius. In other cases, the optical depth is on the same order as the radius, and the intensity emitted is somewhere between the optically thick and thin cases. The equations above can be adopted, given the specific materials optical property characteristics for the specific particle conditions (e.g. temperature).

Another implementation of this PSF sensor allows velocity to also be determined. Instead of using the columnar array of 2048 photo-detectors, a two dimensional full frame image sensor consisting of 1536 columns of 2048 photo-detectors is used. The integration time (exposure time) of the image sensor is then set so that the image of a single particle projected on the array would pass through some but not all of the 1536 columns. The particle velocity could then be measured by counting the number of columns the particle illuminates, and therefore the distance traveled, during the fixed integration time.

Figure 16:
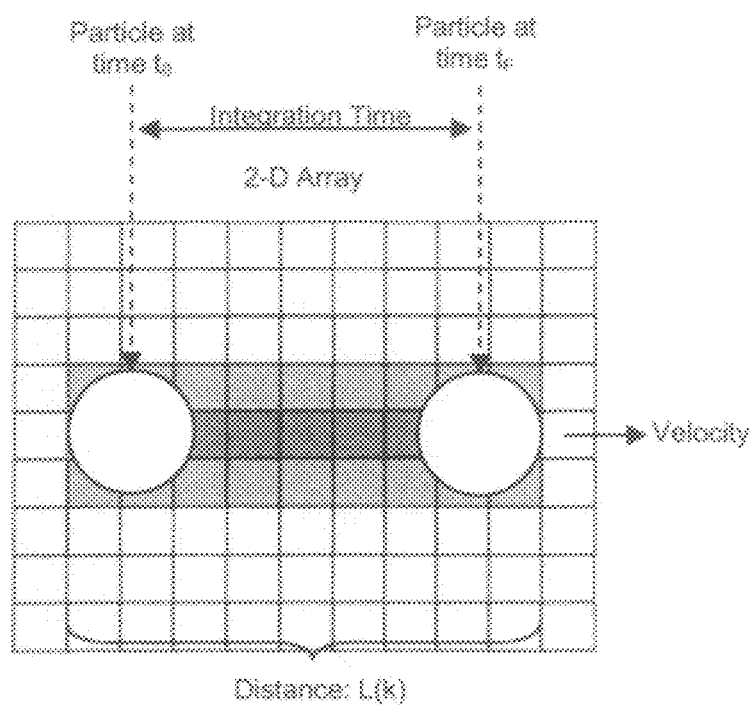
FIG. 16 is a schematic diagram showing the projection of the particle traversing a two dimensional photo-detector array, showing the light received by each pixel as the projection of the particle moves across the array during the exposure time.

The scheme is illustrated in FIG. 16, where the distance traversed, L(k), is measured over some known integration time. Thus the velocity of the measured particle is given by:

$$v = L(k)/\text{integration time} \qquad \text{(eqn. 19)}$$

Figure 17:
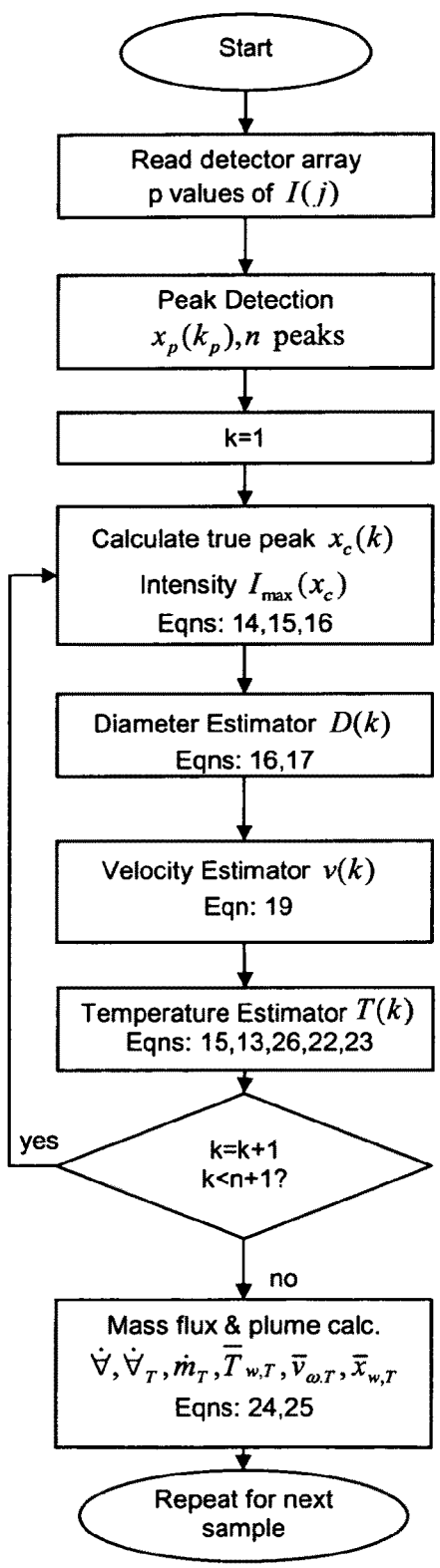
FIG. 17 is a flow chart for a computer program similar to the flow chart of FIG. 15 implemented for a two dimensional array with an additional box for determining particle velocity.

The velocity algorithm can be included into the diameter and temperature algorithm as shown in FIG. 17, where one calculates the velocity before calculating the temperature of the particle. Since the diameter is based on a normalized intensity measurement, an absolute intensity level is not needed. In FIG. 16, the particle is imaged over the integration time, and the velocity can be related to the position of the particle at T(o) until the final time at the end of the sample period.

The algorithm is illustrated in FIG. 17. The program starts by reading data from all the photo-detectors in array 58 during the time interval, as shown in box 120. P is the number of photo-detectors in columnar array 58, i.e. the number of pixels. That array has an index j which corresponds to 1 through P pixels. Then the program determines the number of peaks n that are observed in that frame, as well as the location and magnitude of each peak, as shown in box 121. The algorithm is applied to all n peaks to measure the diameter, peak location, and particle temperature, controlled by boxes 122 and 127. Box 123 determines both the location of the peak and the peak intensity, utilizing eqns. 14-17. The corresponding particle diameter is determined in box 124 based on eqns. 16 and 17. Next, box 125 determines the velocity of the particle based on eqn 19. Then the temperature is calculated in box 126, using equations 15, 13, 26, 22, and 23. The mass flux, centroid position, and other characteristics of the particles and plume are calculated, per equations 24 and 25, as shown in box 128. The process is repeated for the next time interval, as shown in box 129.

One limitation of the previous analysis algorithms is that the observed intensities are dependent on the speed of the particle. Thus, the faster the particle moves, the less time it spends over the array, and thus the smaller the observed intensity.

Considering the peak intensity of the previous method, where x=x, in eqn. 5-18. The dependence on velocity can be expressed as:

$$I_p = F(v) * C_1 * 2R * T^4 \qquad \text{(eqn. 20)}$$

Where F(v) is a factor that accounts for the fact that particles with different velocities will have different times spent over the array, and therefore different intensity. Specifically, F(v) corresponds to the time spent over the array. For a particle with a diameter of 2R, and for pixel of width Δx, and particle velocity of v, this factor is given by:

$$F(v) = (2R + \_x)/v \qquad \text{(eqn. 21)}$$

The faster the particle, the smaller the intensity signal.

The solution is to normalize the intensity (at each pixel) by the time spent over it, which is proportional to the inverse of the velocity. Thus, one should use an intensity corrected for variations in velocity in the previously described algorithms such as represented by:

$$\text{Intensity}_{corrected} = \text{Intensity} * C_v \qquad \text{(eqn. 22)}$$

Where $C_v$, is a velocity correction factor proportional to the particle speed, and inversely proportional to the particle transit time, such as:

$$C_v = V_{particle} \qquad \text{(eqn. 23)}$$

This correction requires measurement of the particle velocity, which is possible using a 2 D array. Note, that in many cases, the magnitude of this error is not significant, especially in cases where the particles are of similar size (mass) and have similar velocities.

By also measuring individual particle velocity, along with temperature and diameter, other critical particle sub-distributions which predict coating properties can be measured. For example, a software algorithm could be made such that the kinetic energy (which is proportional to the square of the velocity times the particle volume) of only molten particles are counted which provides an indication of coating porosity since it affects the spreading of the particle on impact with the substrate.

An algorithm is used to identify and measure the streak lengths of individual particles to calculate particle velocity. The algorithm can be implemented using a standard image processing routine, for example a routine that comes with National Instruments vision software modules. The image processing routine determines the streak length, and therefore the distance traveled during the fixed exposure time. The velocity is determined from this distance divided by the exposure time. Reducing integration time will reduce overlaps of two adjacent particles and two particles whose trajectories cross, improving the calculation. The algorithm also identifies and reject particles whose trajectories extend beyond the edge of the array since the velocity of these particles is indeterminate.

Only particles with a temperature or a diameter above or below a threshold can be included to create sub-distributions of the particles states. For example, summing the volume per unit area per second of all particles that have a temperature above the melting temperature provides an estimate of coating deposition rate. This sub-distribution is termed "molten volume flux".

By detecting the peaks crossing a spatially resolved line, the particle location is also known. Therefore the spatial distribution of particle-state sub-distributions can be measured. For example, one can calculate the averaged position of the particle flux, weighting them by the volume (or mass). This corresponds to the spatial distribution of molten volume flux, and can be called the molten flux centroid. Parameters of this spatial distribution such as centroid and width could be used to indicate aspects of coating deposition.

In general, we can define the average for a quantity Z as:

$$\overline{Z} = \frac{\sum (W_i * Z_i)}{\sum W_i} \quad \text{(eqn. 24)}$$

Where $Z_i$ is the measured variable, $\overline{Z}$ is the averaged quantity, and $W_i$ is the weighting factor.

A number of different weighting factors can be used
Number weighting: $W_i=1$
Area weighting: $W_i=R_i^2$
Volume or mass weighting: $W_i=R_i^3$
where $R_i$ represents the radius of the $i^{th}$ particle. These averages can be selected for individual samples of the arrays, or for some user specified number of samples. Other weighting factors can be used however, depending on the characteristics of the particle characteristics one is trying to capture.

A number of different particle state quantities that can be averaged using these weighting factors including: particle temperature, T, particle velocity, v, and particle position, $x_c$ (referred to as centroid position).

One can also report these averages in terms of sub-distributions, such as temperature above (or below) a certain threshold temperature $\overline{T}_T$ or $\overline{v}_T$ or $\overline{x}_{c,T}$, where the temperature can be selected to refer to those that are molten or non-molten.

The following is a table showing what variables are of interest in terms of using a threshold temperature to indicate the state/quantity of molten, non-molten, and in some case, complete set of particles, for different sort of averaging schemes.

|  | Molten | Non-molten | All |
| --- | --- | --- | --- |
| $\dot{m}$ | X | X | X |
| $\overline{x}_W$ | X | X | X |
| $\overline{T}_W$ | X | X | X |
| $\overline{v}_W$ | X | X | X |

Because plasma spray is used in a variety of different applications with users with varied levels of need, sophistication, and resources, the PSF can be used in a variety of different configurations to meet the different needs. Each configuration offers additional functionality that is designed to provide additional performance depending on the needs of the specific process application. The PSF can be used as a Plasma Deposition Sensor, (PDS), which can be used in either manual or automatic control systems, and additional capabilities can be added which will enable measurement continuously during torch operation, as well as determining the velocity of the molten particles.

Plasma Deposition Sensor (PDS): The PDS includes the abilities of the PSF sensor to measure molten mass flux, and adds the ability to determine molten fraction and molten centroid position. These additional outputs can be calculated from the particle flux data that is obtained by the PSF, and only results in a minimal increase in computational requirements. The PDS sensor can be used to provide a richer set of data for making go/no-go decisions, provide the basis for limited operator adjustment to bring the torch back into a specified window, and also serve as the sensor for real-time control implementation.

To calculate the mass flux for each frame, one calculates the volume for each of the "n" particles observed in the frame, sums the volumes and divides by the exposure time to obtain the volume flux rate for that exposure time. Mass flux rate is proportional to the volume flux rate. Since large fluctuations can occur in many deposition processes, an averaged mass flux is typically more useful, where one would average measured mass flux rates of a specified number of exposure times together. By specifying a temperature threshold to be the melting temperature, the molten volumetric flux rate and molten mass flux rate can similarly be determined. Based on the measured particles in each sample of the array, the total V(l) and qualified, $V_T(l)$, volume mass fluxes are given by:

$$\text{total volume flux } \dot{V}(l) = \frac{\sum d_i^3}{t_{int}} \quad \text{molten volume flux } \dot{V}_T(l) = \frac{\sum d_{T,i}^3}{t_{int}} \quad \text{(eqn. 25)}$$

where $\dot{V}(l)$ is the volume flux rate measured for sample l of the array for all particles measured during the integration time ($t_{int}$), $\dot{V}_T(l)$ is the volume flux above (or below) a threshold temperature, and $d_{T,i}$ is the diameter of the $i^{th}$ particle observed in the array during the integration time which is above a threshold temperature T. Note, that the value $\dot{V}$ can be averaged over different frames to eliminate the high frequency fluctuations of the molten volume flux that can not be easily controlled.

One way to use the PSF and PDS sensors is to use the sensor so that the robotically actuated torch is moved to the predefined sensing position in front of the stationary sensor during measurements. However, this intermittent sensing arrangement may not perform well for some production spraying conditions since it can miss variations that can occur between scheduled sensing times, such as those caused by sudden changes in the torch reattachment point.

Research described in the paper by Chenhuan Cui, "Experimental and Modeling Analyses of Plasma Spray Non-linearities for Advanced Process Control Design", Ph.D. Thesis, January 2007, Boston University, College of Engineering, and the paper by Leblanc, L., C. Moreau and P. Gougeon, "Long-term stability of plasma spraying: study on the evolution of the in-flight particle state, coating microstructure, voltage and acoustic signatures", in Proc. United Thermal Spray Conference, E. Lugscheider and P. A. Kammer (Eds.), Dusseldorf, Germany, 17-19 Mar. 1999, p. 306-311, has shown that variation occurs over a wide range of time scales. Because torch drift typically changes the process gradually over time it can be detected and mitigated by examining the plume between spraying parts. However, there are other variations in which the process suddenly jumps to another state. This second type of variation has a very short timescale, and cannot be corrected with intermittent viewing of the torch.

The PSF can be adopted to travel with the torch, so that all variations can be corrected as they happen, and not just between parts. In this embodiment, the sensor is mounted on the torch, where it is capable of continuous operation, even when parts are being sprayed, so that the deposition rate can be monitored to capture variations that occur during spraying of a single part as well as the part-to-part variations. This provides a significant advance compared to the traditional intermittent monitoring approach, allowing feedback control of thickness on different locations of a specific part.

Torch mounting: One approach for torch mounting involves side mounting to the torch with an angled mirror, as shown in FIG. 18. This approach reduces the possibility of interference from a sensor mounted ahead of the torch and provides the most options for adjusting the position and orientation of the imaged plane.

Continuous monitoring algorithm: continuously monitoring particles poses several key challenges due to several potential sources of interference that could decrease signal integrity and reduce the accuracy of particle state measurement. These include: interference between the imaged plane and the part (especially for curved parts); interference from particles which do not deposit on the target part but instead deflect off the target part back into the sensor measurement plane; and interference from light emitted by the particles and plasma reflecting off the target part back to the sensor. Solutions to these problems include the use of an optical filter tuned to block the wavelength of light emitted by the plasma, identifying and rejecting signals associated with reflected light and scattered particles, and using a measurement plane sufficiently upstream of the part to avoid blockage by the part.

Besides implementing with a black and white intensity array, one could also use color based linear arrays, such as the Basler L301kc, or L304kc. These arrays are comprised of arrays of 2048 rows, but with 3 columns, where each column represents a different color, such as red R, green G, and blue B, as shown in FIG. 19*a*. An intensity as a function of position profile is obtained for the projection of each moving particle as shown in FIGS. 19*b*-19*d*. The advantage is that one can then use the different spectrum of each color to help in estimating the temperature of the observed particle. This is related to the technique of using multi-color spectrometry (e.g. 2 color) to determine the temperature, and helps to minimize the sensitivity to the poorly known emissivity of the substance. Standard numerical analysis techniques for this estimation scheme would be employed. The performance of these systems improves if a narrower band pass is used for each color. The limitation, however is that this also reduces the intensity seen by the photo-detectors. Alternatively, a 3CCD array that uses a beam splitter to image the light onto 3 separate arrays can be used. Each would have a color filter.

The sensing concept described above for moving particles can also be adopted to work for non-moving particles. In this case, instead of the particles moving over a linear array, an array composed of rectangular pixels would be used for objects that would have a projected image smaller then the size of the array. Instead of using a 1 D array, where the pixels would have one dimension significantly larger than the other, a 2 D array could be used, if the intensities of columns of the array would be added together and treated as one "pixel" output. The same equations as outline (eqn 5-18) would be applicable. The same formulation of using the spatially varying intensity collected over a sample time (which is integrated energy), would apply.

Some emerging applications in particle spray coating use particles which are not at sufficient temperature to produce detectable radiant light. In such situations, another embodiment provides an external light source to illuminate the particles. For example, a laser could be used to illuminate particles in the sensor measurement area. This would enable measurement of particle diameter, velocity, and relative spatial distribution of particles throughout the plume.

A variety of calibration schemes are available for the PSF and PDS sensors. The basic calibration for diameter can be performed with a rotating disk with a known size pinhole. In addition, by varying the voltage into the light that shines behind the pinhole, one is also changing the temperature of the bulb observed by the sensor. Thus, one has a straightforward way to implement both diameter and temperature calibration.

Figure 20:
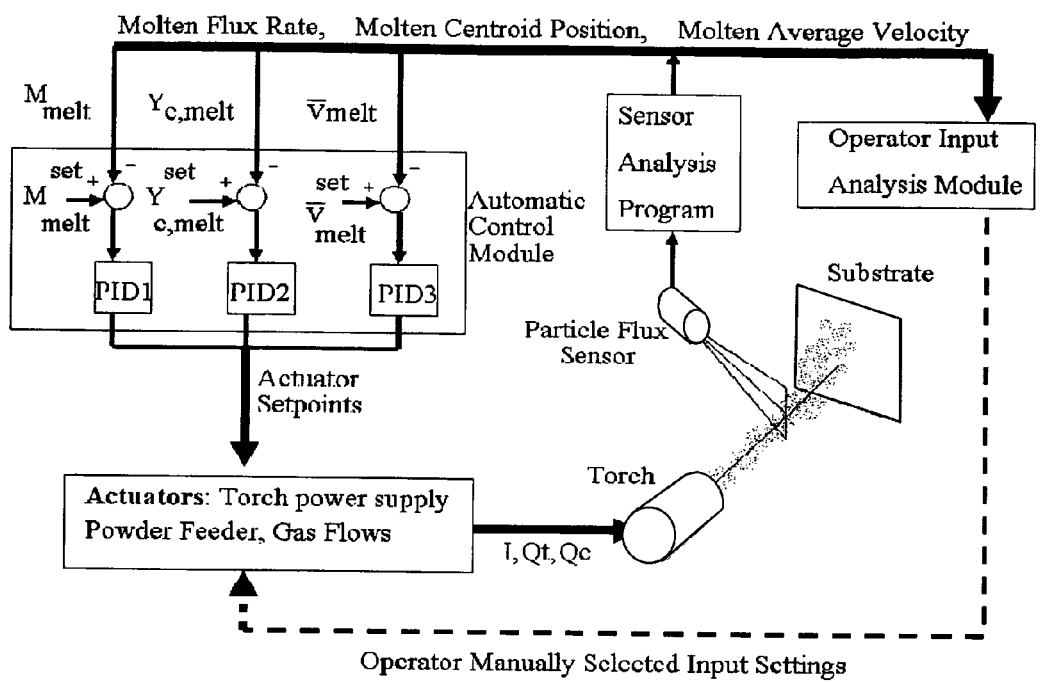
FIG. 20 is a schematic and a block diagram showing how the sensor of the present application is used in a closed loop control system.

Control Applications: The PDS can be used in two manners for control: a) for manual operator adjustment, and b) and for automatic real-time control. Sensor feedback to an operator can provide significant value, increasing yield, but achieving only modest variation reduction, since it is difficult for an operator to adjust multiple inputs frequently to maintain optimized deposition conditions. The real-time control use of the PSF/PDS sensor can automatically adjust multiple process inputs based on the sensor feedback in order to minimize the affects of the wide source of variations that act on this process. This use of the sensor has the potential to lower variation significantly and enables more sources of savings, such as reducing material waste by setting set-points lower. These concepts are illustrated in FIG. 20. Here the PSF sensor provides information either to an operator, for the operator to make manual adjustments to the torch inputs, or to an automatic feedback control system, wherein the control structure (relation of measurements to actuators), and the tuning of the control algorithms, has been determined, as described in U.S. Pat. No. 6,967,304, issued Nov. 22, 2005, incorporated herein by reference.

While the disclosed methods and systems have been shown and described in connection with illustrated embodiments, various changes may be made therein without departing from the spirit and scope of the invention as defined in the appended claims.

The invention claimed is:

1. A method of measuring parameters of a particle comprising:
   a. providing a particle moving substantially in a first direction, wherein said particle has a first portion and a second portion, wherein said first portion is different from said second portion;
   b. providing a column of photo-detectors including a first photo-detector and a second photo-detector, wherein said first photo-detector measures amount of light received by said first photo-detector and said second photo-detector measures amount of light received by said second photo-detector, wherein a direction along said column of photodetectors defines a second direction, wherein said second direction is substantially perpendicular to said first direction, wherein a direction across said column of photodetectors is substantially parallel to said first direction;
   c. providing an optical system, and using said optical system for projecting light from said particle onto said column of photo-detectors, wherein said optical system is positioned and said column of photo-detectors is oriented so said optical system projects light from said first portion onto said first photo-detector and light from said second portion onto said second photo-detector;
   d. taking a measurement with said first photo-detector and taking a measurement with said second photo-detector as said projected light from said particle completely traverses across said column, wherein said first photo-detector measurement includes said amount of light received from said first portion of only one said particle and wherein said second photo-detector measurement includes said amount of light received from said second portion of said only one said particle; and e. using said first and said second photo-detector measurements to determine at least one from the group consisting of temperature and diameter of said one said particle.

2. A method as recited in claim 1 wherein said column of photo-detectors and said optical system define a measurement volume, further comprising providing a number of particles traveling across said measurement volume in an interval of time and determining said number of particles traveling across said measurement volume during said interval of time based on data from said column of photo-detectors.

3. A method as recited in claim 1 wherein said particle is traveling in a first direction, wherein said optical system is located to collect light traveling along a second direction substantially perpendicular to said first direction.

4. A method as recited in claim 3, further comprising determining location of said particle along said second direction from said intensity of light as a function of position data.

5. A method as recited in claim 1, further comprising using measurements by said photo-detectors of said column of photo-detectors during an interval of time to provide an amount of light as a function of position profile.

6. A method as recited in claim 5, further comprising using at least one from the group consisting of said amount of light as a function of position profile and a second derivative of said amount of light as a function of position profile to determine at least one from the group consisting of diameter, temperature, and particle location.

7. A method as recited in claim 5, wherein said column includes additional photo-detectors, further comprising moving a plurality of particles in said first direction and further comprising simultaneously recording amount of light as a function of position profiles for a plurality of said particles with said additional photo-detectors in said column of photo-detectors.

8. A method as recited in claim 7, further comprising determining both diameter and temperature of each of said particles from said amount of light as a function of position profiles.

9. A method as recited in claim 7, further comprising determining a weighted average of at least one from the group consisting of temperature and position for said plurality of particles wherein said average is weighted with at least one from the group consisting of particle volume, particle cross sectional area, and number of particles.

10. A method as recited in claim 7, further comprising determining at least one from the group consisting of particle volume flux per second, particle area flux per second, particle number flux per second, and particle mass flux per second.

11. A method as recited in claim 10, further comprising determining said at least one flux per second of for particles that have a property that is at least one from the group consisting of above a threshold and below a threshold.

12. A method as recited in claim 11, wherein said property includes at least one from the group consisting of having a temperature above a temperature threshold, having a volume above a volume threshold, and having a velocity above a velocity threshold.

13. A method as recited in claim 12, wherein said temperature threshold is indicative of molten particles.

14. A method as recited in claim 7, wherein said plurality of particles includes molten particles, further comprising determining centroid position of said molten particles.

15. A method as recited in claim 7, wherein said plurality of particles includes molten particles, further comprising determining molten volume flux per second from said amount of light of light as a function of position data.

16. A method as recited in claim 1, wherein said column of photo-detectors is part of a two dimensional array of photo-detectors, wherein one dimension of said two dimensional array is along said first direction, further comprising determining particle velocity from said amount of light of light as a function of position data along said first direction.

17. A method as recited in claim 1, further comprising a third photo-detector, wherein said third photo-detector is sensitive to a range of light frequencies different from said first photo-detector, further comprising using amount of light measured by said first photo-detector and amount of light measured by said third photo-detector to determine particle temperature.

18. A method of measuring parameters of a particle comprising:

a. providing a plurality of particles moving substantially in a first direction;

b. providing a column of photo-detectors;

c. providing an optical system and using said optical system for projecting light from at least one of said particles onto said column of photo-detectors, wherein said projected light from each of said at least one of said particles falls on a plurality of said photo-detectors of said column of photo-detectors;

d. collecting said light with said plurality of photo-detectors for an interval of time and measuring amount of light collected by each of said photo-detectors during said interval of time, wherein said interval of time is set to avoid overlapping projected light from different particles on any of said photodetectors; and e. using said measurement of light collected during said interval of time to determine at least one from the group consisting of temperature and diameter of said at least one of said particles.

19. A method of measuring parameters of a particle comprising:

a. providing an array of photo-detectors including a first photo-detector and a second photo-detector;

b. providing an optical system that projects light coming from a measurement volume onto said array of photo-detectors;

c. providing a particle moving across said measurement volume, wherein said particle has a first portion and a second portion, wherein said first portion is different from said second portion, wherein said particle is moving substantially in a first direction, wherein said optical system is positioned and said array of photo-detectors is oriented so said optical system projects light from said first portion onto said first photo-detector and light from said second portion onto said second photo-detector;

d. receiving light from said measurement volume with said array of photo-detectors for an exposure time, wherein amount of light received from said first portion is measured by said first photo-detector and amount of light received from said second portion is measured by said second photo-detector wherein said first photo-detector collects light from only one particle during said exposure time and wherein said second photo-detector collects light from only said one particle during said exposure time;

e. using amount of light measured by said first photo-detector and amount of light measured by second photo-detector to determine at least one from the group consisting of temperature and diameter of said particle.

20. A method as recited in claim 19, further comprising using amount of light measured by said first photo-detector and amount of light measured by second photo-detector to determine position of said particle.

21. A method as recited in claim 19, further comprising using amount of light measured by said first photo-detector and amount of light measured by second photo-detector to determine diameter of said particle.

22. A method as recited in claim 19, further comprising providing a plurality of particles moving in said first direction in said measurement volume, wherein said array of photodetectors further comprises additional photo-detectors, and determining number of particles crossing said measurement volume in said exposure time from said amount of light measured by a plurality of said photo-detectors for each particle.

23. A method as recited in claim 22, further comprising determining particle volume flux per second from said amount of light measured by a plurality of photo-detectors for each particle.

24. A method as recited in claim 22, further comprising determining at least one from the group consisting of particle volume flux per second, particle area flux per second, particle number flux per second, and particle mass flux per second of particles that have a temperature that is at least one from the group consisting of above a threshold and below a threshold.

25. A method as recited in claim 24, wherein said threshold is indicative of molten particles.

26. A method as recited in claim 22, wherein said plurality of particles includes molten particles, further comprising determining centroid position of said molten particles.

27. A method as recited in claim 22, wherein said plurality of particles includes molten particles, further comprising determining molten volume flux per second from said amount of light of light as a function of position data.

28. A method as recited in claim 19, wherein said array consists of a one dimensional array.

29. A method as recited in claim 19, wherein said array consists of a two dimensional array, further comprising determining particle velocity from said amount of light of light as a function of position data.

30. A method as recited in claim 19, wherein said optical system is located to collect light traveling perpendicular to said first direction.

31. A method as recited in claim 19, wherein said array is two dimensional, wherein one said dimension of said array extends along said first direction, further comprising determining velocity of said particle.

32. A method as recited in claim 31, wherein said velocity is determined from number of photo-detectors along said first direction that receive light from said particle during said exposure time.

33. A method as recited in claim 19, wherein said array of photo-detectors includes a third photo-detector, wherein said third photo-detector is sensitive to a range of light frequencies different from said first photo-detector, further comprising using amount of light measured by said first photo-detector and amount of light measured by said third photo-detector to determine particle temperature.

34. A method as recited in claim 1, wherein said photo-detectors are sensitive to substantially the same range of light frequencies.

35. A method as recited in claim 18, wherein said plurality of photo-detectors of said column of photo-detectors are all sensitive to substantially the same range of light frequencies.

36. A method as recited in claim 19, wherein said first photo-detector and said second photo-detector are sensitive to substantially the same range of light frequencies.

* * * * *